US010102622B2

(12) United States Patent
Ishikawa et al.

(10) Patent No.: US 10,102,622 B2
(45) Date of Patent: Oct. 16, 2018

(54) PROCESSING APPARATUS, PROCESSING METHOD, AND NON-TRANSITORY COMPUTER-READABLE STORAGE MEDIUM

(71) Applicant: CANON KABUSHIKI KAISHA, Tokyo (JP)

(72) Inventors: Ryo Ishikawa, Kawasaki (JP); Takaaki Endo, Urayasu (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/202,728

(22) Filed: Jul. 6, 2016

(65) Prior Publication Data

US 2016/0314587 A1    Oct. 27, 2016

Related U.S. Application Data

(63) Continuation of application No. PCT/JP2014/005893, filed on Nov. 25, 2014.

(30) Foreign Application Priority Data

Jan. 10, 2014  (JP) .................................. 2014-003698

(51) Int. Cl.
*G06T 7/00* (2017.01)
*A61B 5/055* (2006.01)
(Continued)

(52) U.S. Cl.
CPC ............ *G06T 7/0012* (2013.01); *A61B 5/055* (2013.01); *A61B 5/4312* (2013.01); *A61B 6/502* (2013.01);
(Continued)

(58) Field of Classification Search
CPC combination set(s) only.
See application file for complete search history.

(56) References Cited

U.S. PATENT DOCUMENTS 4,570,638 A * 2/1986 Stoddart .............. A61B 5/0091
356/432
5,709,206 A * 1/1998 Teboul ................. A61B 8/0825
128/915
(Continued)

FOREIGN PATENT DOCUMENTS

CN    101017575 A    8/2007
CN    101203170 A    6/2008
(Continued)

OTHER PUBLICATIONS

Jul. 18, 2017 European Search Report in European Patent Application No. 14878217.0.
(Continued)

*Primary Examiner* — Tsung-Yin Tsai
(74) *Attorney, Agent, or Firm* — Fitzpatrick, Cella, Harper & Scinto

(57) ABSTRACT

A processing apparatus obtains a contour of a region of interest of a target object and a reference point on the contour from an image of the target object, calculates a distance and an azimuth at an arbitrary position on the contour from the reference point, and generates normalization transformation information for transforming a shape of the region of interest of the target object to a predetermined reference shape based on the distance and the azimuth.

13 Claims, 19 Drawing Sheets

(51) Int. Cl.
*A61B 5/00* (2006.01)
*A61B 6/00* (2006.01)
*A61B 8/08* (2006.01)
*G06K 9/00* (2006.01)
*G06K 9/46* (2006.01)
*G06K 9/52* (2006.01)
*G06K 9/62* (2006.01)
*G06T 7/60* (2017.01)
*G06T 7/33* (2017.01)
*G06T 7/70* (2017.01)
*G06T 7/13* (2017.01)

(52) U.S. Cl.
CPC .......... *A61B 6/5211* (2013.01); *A61B 8/0825* (2013.01); *A61B 8/483* (2013.01); *A61B 8/5207* (2013.01); *G06K 9/00369* (2013.01); *G06K 9/4604* (2013.01); *G06K 9/4671* (2013.01); *G06K 9/52* (2013.01); *G06K 9/6215* (2013.01); *G06T 7/13* (2017.01); *G06T 7/33* (2017.01); *G06T 7/60* (2013.01); *G06T 7/70* (2017.01); *A61B 2576/02* (2013.01); *G06K 2009/4666* (2013.01); *G06T 2207/10116* (2013.01); *G06T 2207/30004* (2013.01); *G06T 2207/30068* (2013.01)

(56) References Cited

U.S. PATENT DOCUMENTS

| | | | |
|---|---|---|---|
| 6,246,782 B1 * | 6/2001 | Shapiro | G06T 7/0012 128/925 |
| 6,633,304 B2 | 10/2003 | Anabuki et al. | |
| 6,636,234 B2 | 10/2003 | Endo et al. | |
| 6,810,152 B2 | 10/2004 | Endo et al. | |
| 6,825,472 B2 | 11/2004 | Endo | |
| 6,950,120 B1 | 9/2005 | Endo et al. | |
| 6,968,084 B2 | 11/2005 | Satoh | |
| 7,035,760 B2 | 4/2006 | Kobayashi et al. | |
| 7,193,636 B2 | 3/2007 | Satoh | |
| 7,454,065 B2 | 11/2008 | Satoh | |
| 7,587,295 B2 | 9/2009 | Satoh | |
| 7,613,356 B2 | 11/2009 | Uchiyama et al. | |
| 7,620,222 B2 | 11/2009 | Oosawa | |
| 7,783,094 B2 | 8/2010 | Collins et al. | |
| 8,620,055 B2 | 12/2013 | Barratt et al. | |
| 2003/0011596 A1 * | 1/2003 | Zhang | G06T 15/506 345/426 |
| 2004/0174386 A1 | 9/2004 | Kotake et al. | |
| 2004/0184646 A1 | 9/2004 | Oosawa | |
| 2006/0050944 A1 | 3/2006 | Takeo et al. | |
| 2006/0274928 A1 * | 12/2006 | Collins | A61B 6/00 382/132 |
| 2007/0260135 A1 * | 11/2007 | Rousson | G06K 9/34 600/407 |
| 2011/0013819 A1 | 1/2011 | Raundahl et al. | |
| 2011/0077523 A1 * | 3/2011 | Angott | A61B 5/0059 600/448 |
| 2012/0014578 A1 * | 1/2012 | Karssemeijer | G06T 7/0012 382/131 |
| 2012/0155734 A1 | 6/2012 | Barratt et al. | |
| 2012/0207368 A1 * | 8/2012 | Ishikawa | G06T 7/0032 382/128 |
| 2012/0230568 A1 * | 9/2012 | Grbic | G06K 9/6211 382/131 |
| 2016/0104280 A1 * | 4/2016 | Buelow | G06T 7/344 382/131 |
| 2016/0155247 A1 * | 6/2016 | Robinson | A61B 8/4254 382/131 |
| 2017/0172485 A1 * | 6/2017 | Makower | A61M 1/06 |

FOREIGN PATENT DOCUMENTS

| | | |
|---|---|---|
| CN | 101373479 A | 2/2009 |
| JP | 2004-283211 A | 10/2004 |
| JP | 2008-086400 A | 4/2008 |
| JP | 2013-501290 A | 1/2013 |
| WO | 2011/015822 A1 | 2/2011 |

OTHER PUBLICATIONS

Asi Elad, et al., "On Bending Invariant Signatures for Surfaces", IEEE Transactions on Pattern Analysis and Machine Intelligence, Oct. 2003, pp. 1285-1295, vol. 25, No. 10, IEEE Computer Society.

Daniel Rueckert, et al., "Automatic Construction of 3-D Statistical Deformation Models of the Brain Using Nonrigid Registration", IEEE Transactions on Medical Imaging, Aug. 2003, pp. 1014-1025, vol. 22, No. 8.

Jun. 28, 2018 Chinese Official Action in Chinese Patent Appln. No. 201480072631.2.

* cited by examiner

PROCESSING APPARATUS, PROCESSING METHOD, AND NON-TRANSITORY COMPUTER-READABLE STORAGE MEDIUM

This application is a continuation of International Patent Application No. PCT/JP2014/005893 filed on Nov. 25, 2014, and claims priority to Japanese Patent Application No. 2014-003698 filed on Jan. 10, 2014, the entire content of both of which is incorporated herein by reference.

TECHNICAL FIELD

The present invention relates to a processing apparatus, processing method, and a non-transitory computer-readable storage medium storing a computer executable program which process medical images obtained by various medical image acquisition apparatuses (modalities) such as a nuclear magnetic resonance apparatus (MRI), an X-ray computed tomography apparatus (X-ray CT), and an ultrasonic diagnostic apparatus (US).

BACKGROUND ART

In the medical field, it is sometimes the case that when a region of interest exists on an image obtained by a given modality, a corresponding region is identified on an image obtained by another modality, and diagnosis is then performed based on the comparison between them. If imaging posture differs between modalities, the shape of the object differs at the times of imaging. This makes it difficult to identify the object. Under the circumstance, attempts have been made to estimate the deformation of an object between modalities (that is, alignment between images accompanying deformation). This makes it possible to estimate the position of a corresponding region based on the position information of a region of interest and to generate an image by deforming one image so as to have the same shape as that of the other image.

NPL 1 discloses a technique of facilitating the comparison between the shapes of an object before and after its deformation by normalizing the shape of the object accompanying deformation. More specifically, there is disclosed a method of calculating the geodesic distance matrix of the surface shape of an object and normalizing the surface shape by using a multidimensional scaling method using the calculated matrix. This method can normalize the shape of an object which deforms without changing the geodesic distance matrix of the object surface so as to allow direct comparison between the shapes of the object before and after the deformation. This makes it possible to easily compare the deformed shapes of an object accompanying deformation and recognize the object based on its shape.

CITATION LIST

Non Patent Literature

NPL 1: A. Elad and R. Kimmel, "On bending invariant signatures for surfaces," IEEE Trans. PAMI, 25(10), 2003

NPL 2: Daniel Rueckert, Alejandro F. Frangi, and Julia A. Shnabel, "Automatic construction of 3-D statistical deformation models of the brain using Nonrigid registration," IEEE Transaction on medical imaging, Vol. 22, No. 8, 2003

SUMMARY OF INVENTION

Technical Problem

Using the method disclosed in NPL 1 can perform normalization between the shapes of an object having a complicated shape before and after its deformation, and hence can relatively easily perform alignment. However, there is a problem that when the shape of an object is relatively monotonous and there are only a small number of land marks and the like which can be associated with each other between deformed shapes, the posture of the object after normalization remains unstable.

The present invention has been made in consideration of the above problem, and has as its object to provide a mechanism which can simply and stably perform normalization between different shapes. In addition, it is an object of the present invention to provide a mechanism which accurately performs alignment between shapes based on normalization.

Solution to Problem

In order to achieve the above object, a processing apparatus according to one aspect of the present invention has the following arrangement. That is, this arrangement includes obtaining means for obtaining a contour of a region of interest of a target object and a reference point on the contour from an image of the target object, calculation means for calculating a distance and an azimuth at an arbitrary position on the contour from the reference point, and normalization means for generating normalization transformation information for transforming a shape of the region of interest of the target object to a predetermined reference shape based on the distance and the azimuth.

Advantageous Effects of Invention

According to the present invention, it is possible to provide a mechanism which can simply and stably perform normalization between different shapes. In addition, it is possible to provide a mechanism which can accurately perform alignment between shapes based on normalization.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF EMBODIMENTS

Figure 1:
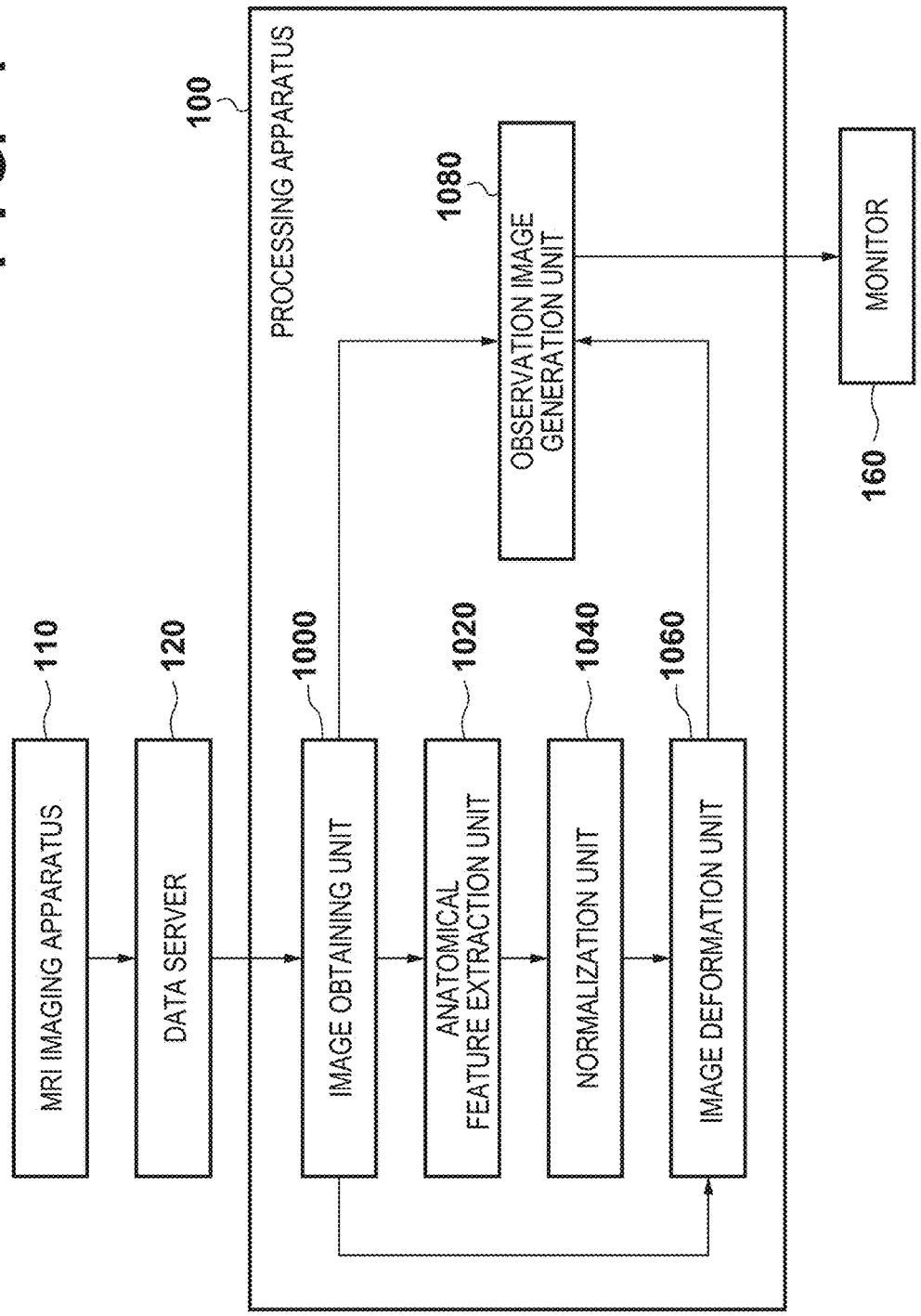
FIG. 1 is a block diagram showing the functional arrangement of a processing system according to the first embodiment.

Embodiments of a processing apparatus and method according to the present invention will be described in detail below with reference to the accompanying drawings. The scope of the present invention is not limited to the examples shown in the drawings.

[First Embodiment]

(Overview of First Embodiment)

When medical images are obtained by imaging the breast of an object as a region of interest in two different types of postures, a processing apparatus according to this embodiment obtains a normalization transformation (normalization transformation information) for transforming each medical image to a reference shape, and performs deformation alignment between the images via the obtained normalization transformation. This normalization transformation is coordinate transformation of the breast of the object, which has been imaged in different deformed states due to different postures, to spaces almost anatomically matching each other.

In this case, the following characteristics concerning the deformation of the breast between the prone position and the supine position are biomechanically known. First, the azimuth with reference to the nipple is basically held on the coronal plane. Second, the geodesic distance with reference to the nipple is basically held on the body surface. Based on these characteristics, a space is assumed, in which azimuths and geodesic distances with reference to the nipple are normalized, and each of the breasts in the different deformed states is transformed to coordinates in the space. This basically absorbs variations in position with the deformation caused between the prone position and the supine position, and can perform transformation to an anatomically common space. Performing deformation alignment between the images via this transformation makes it possible to implement alignment with higher accuracy than directly performing deformation alignment between the original images.

This embodiment is configured to extract the contour of the breast of an object from each of obtained medical images and calculate a normalization transformation for the coordinate transformation of the shape of the breast to a rectangular shape as a reference shape based on a reference point on the contour. Although the following will describe a case in which an object is the breast of a human body in the supine position and the prone position, the posture and region of the object are not specifically limited. In addition, this embodiment will exemplify a case in which a three-dimensional MRI image is used as a medical image. However, a medical image to be used is not limited to an MRI image, and another type of three-dimensional image may be used. For example, the embodiment can be applied to X-ray CT images, 3D ultrasonic images, and PET images.

(Functional Arrangement)

FIG. 1 is a block diagram showing the arrangement of a processing system according to this embodiment. As shown in FIG. 1, a processing apparatus 100 according to the embodiment includes an image obtaining unit 1000, an anatomical feature extraction unit 1020, a normalization unit 1040, an image deformation unit 1060, and an observation image generation unit 1080. The processing apparatus 100 is connected to a data server 120 and a monitor 160. An MRI imaging apparatus 110 is an apparatus which obtains an image by obtaining information concerning a three-dimensional region inside an object as a human body by a nuclear magnetic resonance method, that is, an MRI image. The MRI imaging apparatus 110 is connected to the data server 120, and transmits the obtained MRI image to the data server 120. The data server 120 is an apparatus which holds the MRI image obtained by the MRI imaging apparatus 110, and transfers the held MRI image to the processing apparatus 100 in response to an instruction from the processing apparatus 100.

Each element constituting the processing apparatus 100 will be described next. The image obtaining unit 1000 inputs an MRI image of an object (target object) imaged by the MRI imaging apparatus 110 to the processing apparatus 100 via the data server 120. The anatomical feature extraction unit 1020 processes the MRI image input by the image obtaining unit 1000 to extract anatomical features of the object. The normalization unit 1040 calculates a transformation for transforming (normalizing) the shape of the object to a reference shape based on the anatomical features of the object extracted by the anatomical feature extraction unit 1020. Normalization will be described in detail later. The image deformation unit 1060 performs alignment between the prone position and the supine position based on the transformation calculated by the normalization unit 1040, and deforms the prone position MRI image to generate a deformed image matching the supine position MRI image. The observation image generation unit 1080 generates an observation image presented to the user by using the MRI image input by the image obtaining unit 1000 and the deformed image generated by the image deformation unit 1060. The observation image generation unit 1080 then outputs the observation image to the monitor 160. The monitor 160 displays the observation image generated by the observation image generation unit 1080.

(Apparatus Arrangement)

Figure 2:
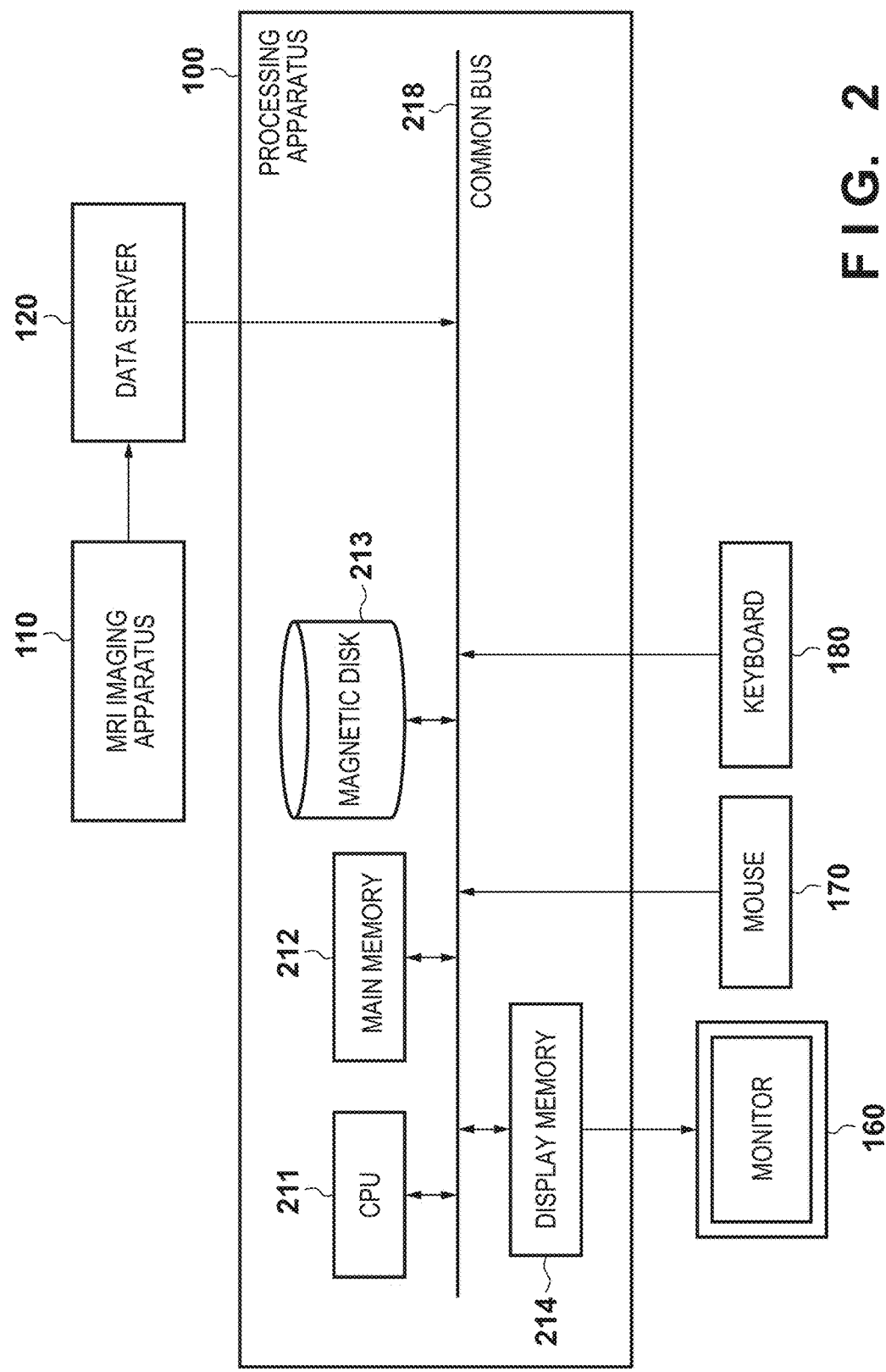
FIG. 2 is a block diagram showing the apparatus arrangement of the processing system according to the first embodiment.

FIG. 2 is a block diagram showing the apparatus arrangement of a processing system according to this embodiment. The processing system according to the embodiment includes the processing apparatus 100, the MRI imaging apparatus 110, the data server 120, the monitor 160, a mouse 170, and a keyboard 180. The processing apparatus 100 can be implemented by, for example, a PC (Personal Computer). The processing apparatus 100 includes a CPU (Central Processing Unit) 211, a main memory 212, a magnetic disk 213, and a display memory 214.

The CPU 211 mainly controls the operation of each constituent element of the processing apparatus 100. The main memory 212 stores control programs executed by the CPU 211, and provides a work area for the execution of programs by the CPU 211. The magnetic disk 213 stores an OS (Operating System), device drives for peripheral devices, various types of application software including programs for the execution of processing (to be described later), and the like. The display memory 214 temporarily stores display data for the monitor 160. The monitor 160 is, for example, a CRT monitor or liquid crystal monitor, and displays an image based on data from the display memory 214. The mouse 170 and the keyboard 180 each are used by the user to perform a pointing input operation and input characters, commands, and the like. The above constituent elements are communicably connected to each other via a common bus 218.

(Processing Procedure)

Figure 3:
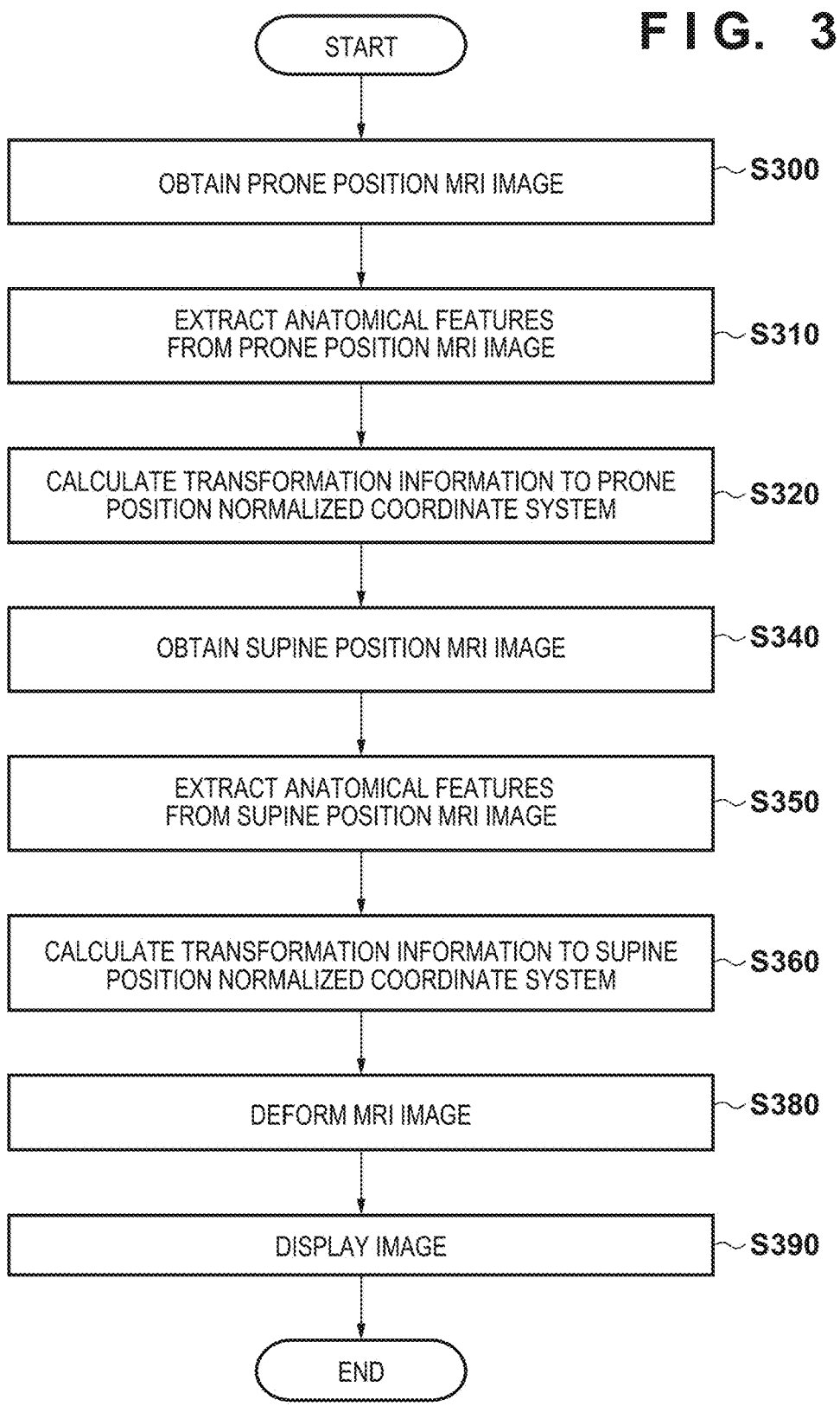
FIG. 3 is a flowchart showing a processing procedure performed by a processing apparatus according to the first embodiment.

Processing performed by the processing apparatus 100 will be described in detail next with reference to the flowchart of FIG. 3. FIG. 3 is a flowchart showing processing executed by the processing apparatus 100 according to this embodiment. In the embodiment, the CPU 211 executes programs stored in the main memory 212 to implement the functions of the respective units. In addition, the result of each process performed by the processing apparatus 100 to be described below is recorded by being stored in the main memory 212. The details of procedures in the respective processing steps shown in FIG. 3 will be sequentially described.

(Step S300) Obtaining of Prone Position MRI Image

In step S300, the image obtaining unit 1000 inputs an MRI image (prone position MRI image) obtained by the MRI imaging apparatus 110 by imaging the breast of an object in the prone position to the processing apparatus 100 via the data server 120. Assume that in this case, the prone position MRI image is three-dimensional volume data, and has a three-dimensional orthogonal coordinate system (has undergone such coordinate transformation) with the direction from the feet to the head of the object being the Z-axis, the direction from the abdomen to the back being the Y-axis, and the leftward direction of the object being the X-axis. In this embodiment, this coordinate system is called a prone position MRI image coordinate system. In addition, the intensity value of a prone position MRI image is expressed as a scalar function $I_p(x)$ with a three-dimensional position x as an argument in the prone position MRI image coordinate system.

(Step S310) Extraction of Anatomical Features from Prone Position MRI Image

In step S310, the anatomical feature extraction unit 1020 extracts anatomical features of the object in the prone position by processing the prone position MRI image obtained in step S300. In this embodiment, anatomical features include the nipple position, body surface shape, the pectoralis major muscle surface shape, and a reference position on the pectoralis major muscle surface of the object.

Figure 4:
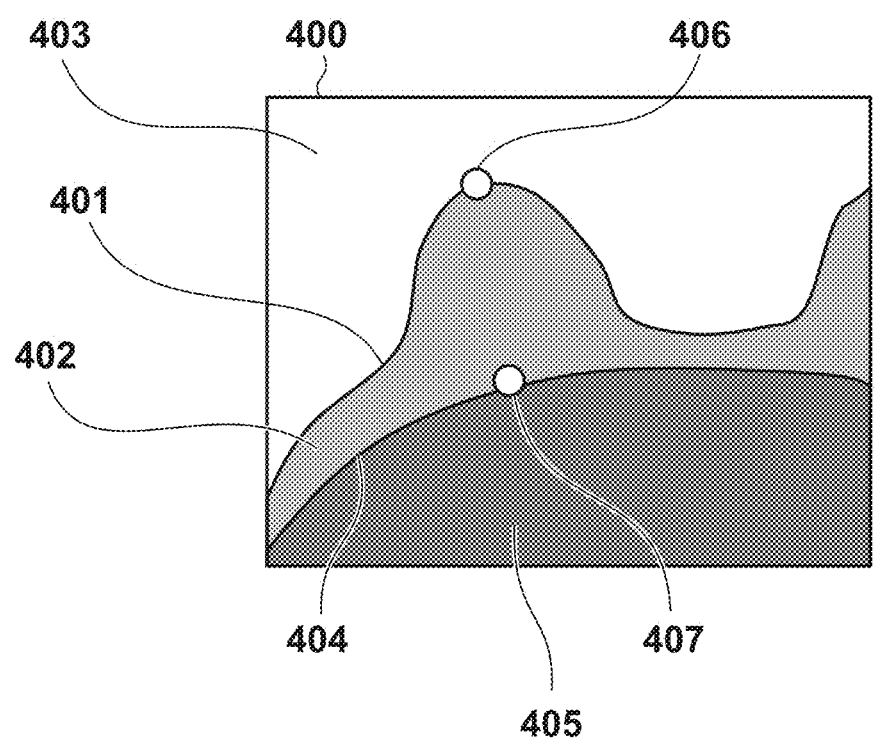
FIG. 4 is a schematic view of an object depicted in the prone position MRI image.

FIG. 4 is a view for explaining anatomical features on a prone position MRI image. Although an actual prone position MRI image is a three-dimensional image, a two-dimensional slice on a three-dimensional image will be described for the sake of convenience of explanation on paper. A prone position MRI image 400 includes an air region 403, a breast region 402, and an inside region 405. A body surface 401 is a set of boundary positions between the air region 403 and the breast region 402, and has a three-dimensional curved surface. A pectoralis major muscle surface 404 is a set of boundary positions between the breast region 402 and the inside region 405, and has a three-dimensional curved surface. In this processing step, the anatomical feature extraction unit 1020 processes the prone position MRI image 400 by a known method such as threshold processing or edge detection to detect the body surface 401. Note however that when detecting the body surface 401, it is not necessary to detect the entire body surface of the object depicted in the prone position MRI image, and it is just required to detect only a body surface relating to a breast region and its peripheral region. In this embodiment, the central position of a breast region in the prone position MRI image is obtained by a user input operation using the mouse 170 or the keyboard 180, and a predetermined range from the central position is set as a processing target.

The body surface 401 is detected by the above method. In this embodiment, a body surface shape as a set of boundary positions between the air region 403 as the body surface and the breast region 402 is expressed as $s_{p,surface,i}$ ($1 \leq i \leq N_{p,surface}$), where $N_{p,surface}$ is the number of positions (points) constituting the body surface shape. Likewise, the pectoralis major muscle surface shape is detected by image processing. In the embodiment, this shape is expressed as $s_{p,pectral,i}$ ($1 \leq i \leq N_{p,pectral}$), where $N_{p,pectral}$ is the number of positions (points) constituting the pectoralis major muscle surface shape. Assume that in this case, the body surface shape and the pectoralis major muscle surface shape are accompanied by connection information between the points constituting them. That is, assume that the body surface shape and the pectoralis major muscle surface shape have both the information of a plurality of points (point groups) representing their positions and information concerning the surfaces formed by the point groups.

The anatomical feature extraction unit 1020 then detects a nipple position. The nipple position can be detected by further processing the body surface shape detected by the above method. For example, local curvatures of the body surface shape are calculated, and a position at which the curvature is maximum can be detected as the nipple position. Alternatively, it is possible to select, as the nipple position, one of all the positions constituting the body surface shape at which the coordinate value on the Y-axis in the MRI image coordinate system is the smallest value (nearest to the abdominal side). In addition, it is possible to detect the nipple position by processing the prone position MRI image. In this embodiment, the detected nipple position is expressed as a three-dimensional coordinate value $x_{p,surface}$. The anatomical feature extraction unit 1020 then detects a reference position on the pectoralis major muscle surface. The processing is executed by, for example, selecting one of all the positions constituting the pectoralis major muscle surface shape which is nearest to the nipple position. In the embodiment, the detected reference position on the pectoralis major muscle surface is expressed as $x_{p,pectral}$.

The anatomical feature extraction unit 1020 then performs coordinate transformation of the prone position MRI image coordinate system such that the nipple position $x_{p,surface}$ detected in the above manner becomes the origin. More specifically, the values $s_{p,surface,i}$, $s_{p,pectral,i}$, $x_{p,surface}$, and $x_{p,pectral}$ obtained by the above processing are translated by $-x_{p,surface}$. With the above processing, anatomical features are extracted in step S310.

Although the method of extracting anatomical features by making the anatomical feature extraction unit 1020 process a prone position MRI image has been described above, this is not exhaustive. For example, the processing apparatus 100 may display a prone position MRI image on the monitor 160 to allow the user to input information concerning anatomical features to the processing apparatus 100 with the mouse 170 and the keyboard 180. In addition, the user may modify and change the anatomical features extracted by image processing by using the mouse 170 and the keyboard 180. Furthermore, the processing apparatus 100 may extract some of anatomical features by image processing and may obtain other anatomical features by input by the user. At this time, some of the anatomical features extracted by image processing may be displayed on the monitor 160. For example, the processing apparatus 100 extracts a body surface shape and a pectoralis major muscle surface shape by image processing, and displays the results on the monitor 160. The user then may input, to the processing apparatus 100, a nipple position and a reference position on the pectoralis major muscle surface by using the mouse 170 and the keyboard 180 while referring to the displayed body surface shape and pectoralis major muscle surface shape.

Figure 5:
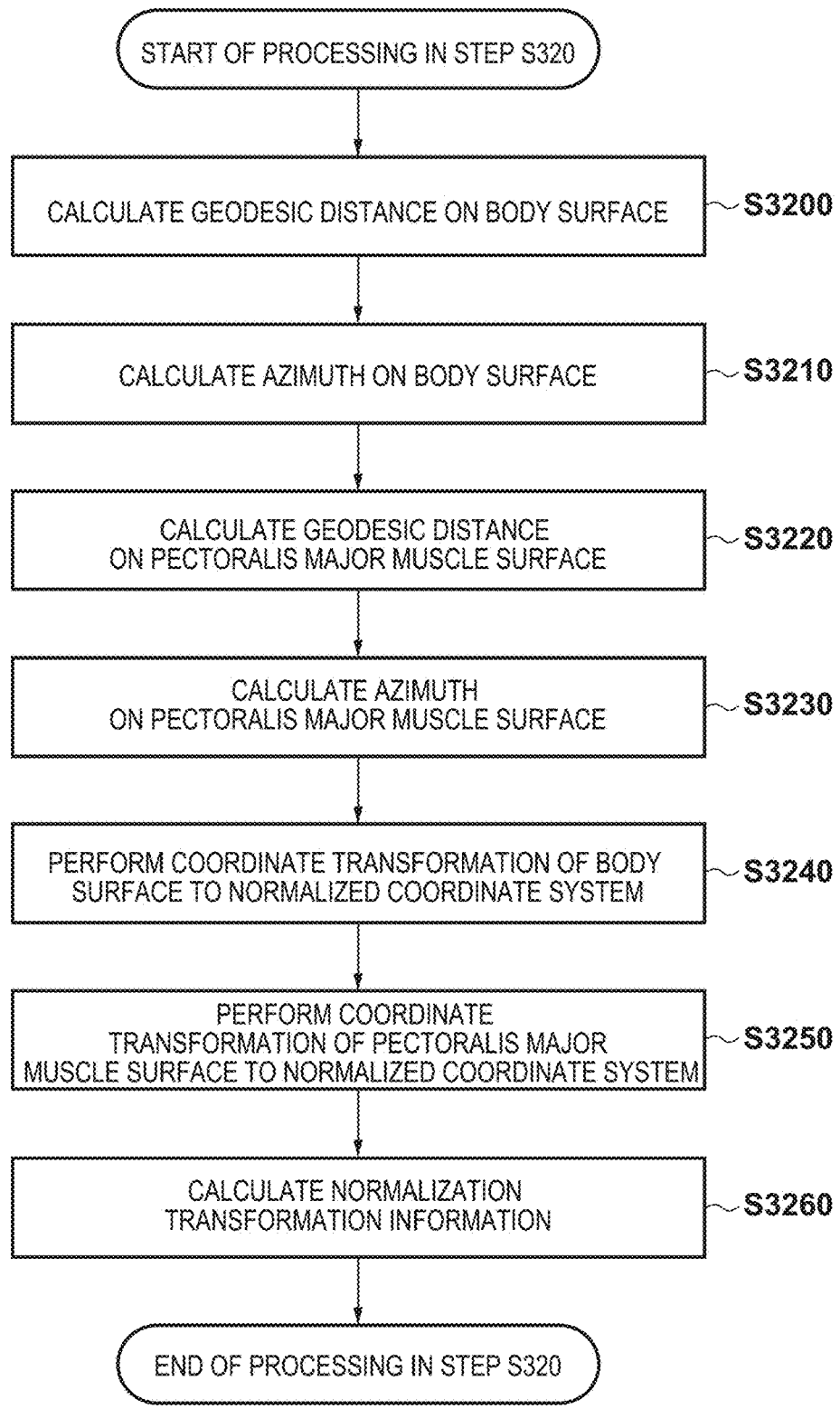
FIG. 5 is a flowchart showing a processing procedure in step S320 according to the first embodiment.

(Step S320) Calculation of Transformation to Prone Position Normalized Coordinate System In step S320, the normalization unit 1040 derives a normalization transformation for transforming the shape of the object in the prone position to a reference shape based on the anatomical features of the object in the prone position which are extracted in step S310. More specifically, the normalization unit 1040 calculates, as information representing transformation from the prone position MRI image coordinate system to the prone position normalized coordinate system, a coordinate transformation function between these coordinate systems. This transformation is performed such that the body surface and the pectoralis major muscle surface in the MRI image coordinate system are located on predetermined surfaces in the prone position normalized coordinate system. In addition, the transformation is performed so as not to impair, as much as possible, an arbitrary structure in the breast region before and after transformation in terms of topology. A specific processing procedure executed in step S320 for the calculation of the above coordinate transformation function will be described in detail below with reference to the flowchart of FIG. 5.

<Step S3200> Calculation of Geodesic Distance on Body Surface

In step S3200, the normalization unit 1040 calculates a geodesic distance at each position constituting the body surface shape of the object in the prone position with reference to the nipple position based on the anatomical features extracted in step S310. That is, the normalization unit 1040 calculates geodesic distances from the nipple at arbitrary positions, of the respective positions constituting the body surface shape, other than the nipple position at which the geodesic distance is 0. Note that it is possible to use any of known methods of calculating geodesic distances. A body surface shape in this embodiment is a set of positions constituting the body surface and is accompanied by information concerning connection between them. It is therefore possible to use, for example, the Dijkstra's Algorithm as a method of calculating geodesic distances. With the above processing, the normalization unit 1040 calculates a geodesic distance $d_{p,surface,i}$ ($1 \leq i \leq N_{p,surface}$) at each position constituting the body surface shape. In this case, the suffix "i" is common to the suffix "i" of the body surface shape $s_{p,surface,i}$ ($1 \leq i \leq N_{p,surface}$), and the geodesic distance at the ith position $s_{p,surface,i}$ of the body surface shape is expressed as $d_{p,surface,i}$.

<Step S3210> Calculation of Azimuths on Body Surface

In step S3210, the normalization unit 1040 calculates an azimuth at each position constituting the body surface shape of the object in the prone position with reference to the nipple position based on the anatomical features extracted in step S310. In this case, an azimuth can be, for example, an azimuth on an X-Z plane in the MRI image coordinate system. In this case, the normalization unit 1040 can calculate an azimuth $a_{p,surface,i}$ [rad] by the calculation represented by equation (1) using an X-coordinate value $x_i$ and a Z-coordinate value $z_i$ of the coordinate value $s_{p,surface,i}$ ($1 \leq i \leq N_{p,surface}$) at each position constituting the body surface shape.

$$a_{p,surface,i} = \tan^{-1}(z_i/x_i) \quad (1)$$

In this case, the suffix "i" is common to the suffix "i" of the body surface shape $s_{p,surface,i}$ ($1 \leq i \leq N_{p,surface}$), and the azimuth at the ith position $s_{p,surface,i}$ of the body surface shape is expressed as $a_{p,surface,i}$.

Note that an azimuth calculation method to be used is not limited to the above method. For example, azimuths can be calculated by the following method. Assume that a vector connecting a nipple position to a reference position on a pectoralis major muscle surface is defined as the Y-axis, and the body axis direction (the direction from the feet to the head) of the object is defined as the Z-axis. Note however that if the Z-axis and the Y-axis are not orthogonal to each other, correction is required. While the cross product direction of the Y-axis and the Z-axis is set as the X-axis, equation (1) may be calculated. The above method has the effect of being able to calculate azimuths on coordinate axes with reference to the posture of an object depicted in an MRI image even if the posture of the object is obliquely tilted in the MRI image coordinate system.

<Step S3220> Calculation of Geodesic Distances on Pectoralis Major Muscle Surface In step S3220, the normalization unit 1040 calculates a geodesic distance $d_{p,pectral,i}$ ($1 \leq i \leq N_{p,pectral}$) with reference to the reference position $x_{p,pectral}$ on the pectoralis major muscle surface at each position $s_{p,pectral,i}$ constituting the pectoralis major muscle surface shape of the object in the prone position based on the anatomical features extracted in step S310. The normalization unit 1040 executes this processing step by applying the same processing as that in step S3200 targeted to the body surface to the pectoralis major muscle surface.

<Step S3230> Calculation of Azimuths on Pectoralis Major Muscle Surface

In step S3230, the normalization unit 1040 calculates an azimuth $a_{p,pectral,i}$ ($1 \leq i \leq N_{p,pectral}$) with reference to the reference position $x_{p,pectral}$ on the pectoralis major muscle surface at each position $s_{p,pectral,i}$ constituting the pectoralis major muscle surface of the object in the prone position based on the anatomical features extracted in step S310. The normalization unit 1040 executes the processing step by applying the same processing as that in step S3210 targeted to the body surface to the pectoralis major muscle surface.

<Step S3240> Coordinate Transformation of Body Surface to Normalized Coordinate System In step S3240, the normalization unit 1040 obtains a transformation for coordinate transformation of the body surface shape of the object in the prone position to a predetermined surface in the prone position normalized coordinate system based on the geodesic distances and azimuths on the body surface calculated in steps S3200 and S3210. More specifically, the normalization unit 1040 calculates a position $s'_{p,surface,i}$ in the prone position normalized coordinate system which corresponds to each position $s_{p,surface,i}$ constituting the body surface shape in the prone position MRI image coordinate system.

Figure 6A:
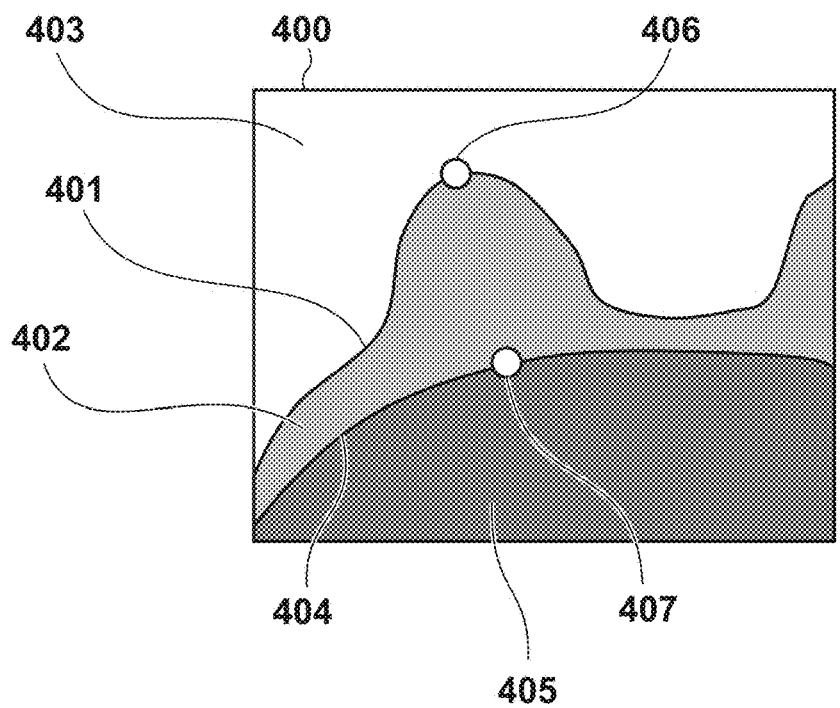
FIG. 6A is a view for explaining a normalized coordinate system according to the first embodiment.
Figure 6B:
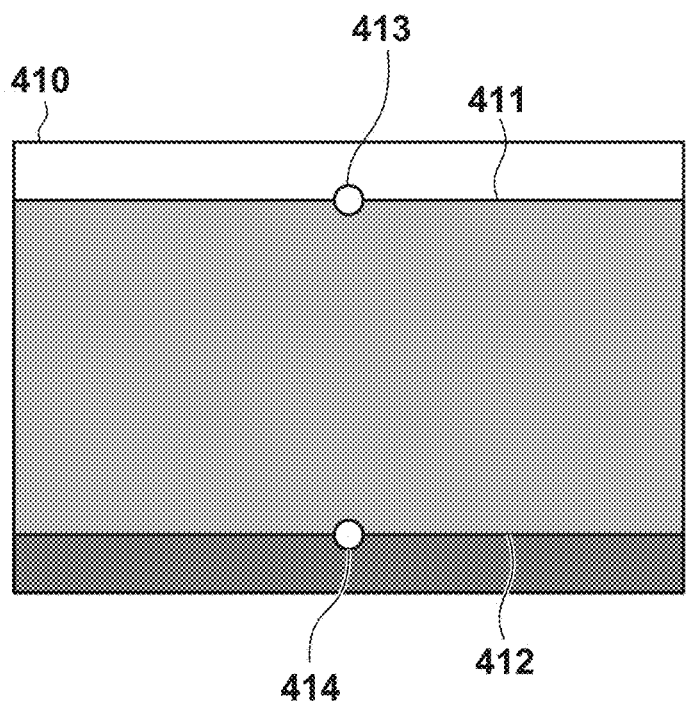
FIG. 6B is a view for explaining a normalized coordinate system according to the first embodiment.

This processing will be described with reference to FIGS. 6A and 6B. FIG. 6A is a schematic view of the breast in the prone position MRI image 400. FIG. 6B is a schematic view of the breast in a prone position normalization space expressed by the prone position normalized coordinate system. For the sake of descriptive convenience, both FIGS. 6A and 6B exemplarily show two-dimensional images. In actual processing, however, each image has a three-dimensional space. For example, the body surface 401 is a curve in FIG. 6A but is a curved surface in actual processing. Likewise, a normalized body surface 411 is a straight line in in FIG. 6B but is a plane in actual processing. In this processing step, as shown in FIG. 6A, the normalization unit 1040 performs coordinate transformation of the body surface 401 whose contour shape is a curved surface to the normalized body surface 411 as a plane on the upper side of a rectangular shape. Assume that the position of a normalized nipple 413 is defined at a predetermined position in the prone position normalized coordinate system. This embodiment will exemplify a case in which the position of the normalized nipple 413 is defined at the origin of the prone position normalized coordinate system A specific processing procedure concerning coordinate transformation of the body surface 401 to the normalized body surface 411 will be described. The body surface 401 is a set of $N_{p,surface}$ points expressed as $s_{p,surface,i}$. At each of these points, the geodesic distance $d_{p,surface,i}$ and the azimuth $a_{p,surface,i}$ have been calculated by the processing in steps S3200 and S3210. In this processing step, the normalization unit 1040 calculates corresponding positions in the prone position normalized coordinate system based on these calculation results. More specifically, the normalization unit 1040 calculates coordinate values by the calculations expressed by equations (2) to (4).

$$x_i = d_{p,surface,i} \cdot \cos(a_{p,surface,i}) \quad (2)$$

$$y_i = 0 \quad (3)$$

$$z_i = d_{p,surface,i} \cdot \sin(a_{p,surface,i}) \quad (4)$$

These calculations indicate that the normalization unit 1040 performs coordinate transformation to all the points on the body surface 401. That is, the normalization unit 1040 performs coordinate transformation of all the points on the body surface 401 in the prone position MRI image coordinate system to points on an x-z plane with y=0 in the prone position normalized coordinate system. In addition, the normalization unit 1040 performs coordinate transformation such that the distances and the azimuths at all the pints with reference to the normalized nipple 413 in the prone position normalized coordinate system match the corresponding geodesic distances and azimuths with reference to a nipple 406 in the prone position MRI image coordinate system. Each position on the normalized body surface in the prone position normalized coordinate system, calculated by the above processing, is expressed as $s'_{p,surface,i}$ ($1 \leq i \leq N_{p,surface}$).

<Step S3250> Coordinate Transformation of Pectoralis Major Muscle Surface to Normalized Coordinate System In step S3250, the normalization unit 1040 obtains a transformation for coordinate transformation of the pectoralis major muscle surface shape of the object in the prone position to a predetermined surface in the prone position normalized coordinate system based on the geodesic distances and the azimuths calculated in steps S3220 and S3230. More specifically, the normalization unit 1040 calculates a position $s'_{p,pectral,i}$ in the prone position normalized coordinate system which corresponds to each position $s_{p,pectral,i}$ constituting the pectoralis major muscle surface shape in the prone position MRI image coordinate system.

This processing will be described with reference to FIGS. 6A and 6B. In this processing step, the normalization unit 1040 executes processing with respect to the pectoralis major muscle surface in the same manner as in step S3240 targeted to the body surface. That is, the normalization unit 1040 executes coordinate transformation of the pectoralis major muscle surface 404 whose contour shape is a curved surface as shown in FIG. 6A to a normalized pectoralis major muscle surface 412 as a plane on the lower side of a rectangular shape. Assume that in this case, the position of a reference point 414 on the normalized pectoralis major muscle surface is defined at a predetermined position in the prone position normalized coordinate system. This embodiment will exemplify a case in which the reference point 414 on the pectoralis major muscle surface is defined at a coordinate value (0, 100, 0) in the prone position normalized coordinate system.

More specifically, the normalization unit 1040 executes processing by calculating equations (5) to (7) with respect to all the points $s_{p,pectral,i}$ on the pectoralis major muscle surface 404. That is, the normalization unit 1040 performs coordinate transformation of all the points to points on an x-z plane flush with the reference point 414 on the normalized pectoralis major muscle surface. At this time, the normalization unit 1040 performs coordinate transformation such that the distances and the azimuths with reference to the reference point 414 on the normalized pectoralis major muscle surface match the geodesic distances $d_{p,pectral,i}$ and the azimuths $a_{p,pectral,i}$ with reference to the reference point on the pectoralis major muscle surface in the prone position MRI image coordinate system.

$$x_i = d_{p,pectral,i} \cdot \cos(a_{p,pectral,i}) \quad (5)$$

$$y_i = 100 \quad (6)$$

$$z_i = d_{p,pectral,i} \cdot \sin(a_{p,pectral,i}) \quad (7)$$

Each position on the normalized pectoralis major muscle surface in the prone position normalized coordinate system, calculated by the above processing, is expressed as $s'_{p,pectral,i}$ ($1 \leq i \leq N_{p,pectral}$).

<Step S3260> Calculation of Normalization Deformation

In step S3260, the normalization unit 1040 calculates, as information representing a transformation from the prone position MRI image coordinate system to the prone position normalized coordinate system, a coordinate transformation function (deformation field) between the coordinate systems. That is, the normalization unit 1040 calculates a dense transformation from the prone position MRI image coordinate system to the prone position normalized coordinate system by spatially interpolating a result group on discrete coordinate transformation of the body surface and the pectoralis major muscle surface obtained in steps S3240 and S3250 to the prone position normalized coordinate system. More specifically, this processing can be implemented by a known interpolation method using a radial basis function, B-spline, or the like. The transformation function from the prone position MRI image coordinate system to the prone position normalized coordinate system, which is calculated in this processing step, is expressed as $\phi_p(x)$ in this embodiment. Note that $\phi_p(x)$ is a function for receiving a positional coordinate value in the prone position MRI image coordinate system as an argument and returning a corresponding positional coordinate value in the prone position normalized coordinate system.

The normalization unit 1040 also calculates a function for receiving a positional coordinate value in the prone position normalized coordinate system as an argument and returning a corresponding position in the prone position MRI image coordinate system, in contrast to $\phi_p(x)$. In this embodiment, this function is expressed as $\phi_p^{-1}(x)$. Assume that in this case, $\phi_p^{-1}(x)$ is defined in a predetermined rectangular region in the prone position normalized coordinate system. The rectangular region is, for example, a rectangular region which encloses all the positions $s'_{p,surface,i}$ and $s'_{p,pectral,i}$.

Note that the transformation functions $\phi_p(x)$ and $\phi_p^{-1}(x)$ calculated by the above method have properties represented by equations (8) to (11).

$$s'_{p,surface,i} = \phi_p(s_{p,surface,i}) \qquad (8)$$

$$s'_{p,pectral,i} = \phi_p(s_{p,pectral,i}) \qquad (9)$$

$$s_{p,surface,i} = \phi_p^{-1}(s'_{p,surface,i}) \qquad (10)$$

$$s_{p,pectral,i} = \phi_p^{-1}(s'_{p,pectral,i}) \qquad (11)$$

The processing in step S320 in this embodiment is executed by the processing in steps S3200 to S3260 described above.

(Step S340) Obtaining of Supine Position MRI Image

In step S340, the image obtaining unit 1000 inputs an MRI image (supine position MRI image) obtained by imaging the breast of the object in the supine position from the data server 120 to the processing apparatus 100. Since the processing can be executed by the same procedure as in step S300 targeted to a prone position MRI image, a detailed description of the processing will be omitted. The obtained supine position MRI image is three-dimensional volume data in a supine position MRI image coordinate system.

(Step S350) Extraction of Anatomical Features from Supine Position MRI Image

In step S350, the anatomical feature extraction unit 1020 extracts anatomical features of the object in the supine position by processing the supine position MRI image obtained in step S340. Since this processing can be executed by applying the same processing as that in step S310 targeted to a prone position MRI image to the supine position MRI image, a detailed description of the processing will be omitted. Note that in the following description, a body surface shape, a pectoralis major muscle surface shape, a nipple position, and a reference point on the pectoralis major muscle surface in the supine position are respectively expressed as $s_{s,surface,i}$ ($1 \leq i \leq N_{s,surface}$), $s_{s,pectral,i}$ ($1 \leq i \leq N_{s,pectral}$), $x_{s,surface}$, and $x_{s,pectral}$.

(Step S360) Calculation of Transformation to Supine Position Normalized Coordinate System In step S360, the normalization unit 1040 derives a normalization transformation for transforming the shape of the object in the supine position to a reference shape based on the anatomical features of the object in the supine position extracted in step S350. More specifically, the normalization unit 1040 calculates, as information representing transformation from the supine position MRI image coordinate system to the supine position normalized coordinate system, a coordinate transformation function between these coordinate systems. This processing can be executed by applying the same procedure as that in step S320 targeted to anatomical features in the prone position to anatomical features in the supine position, and hence a detailed description of the processing will be omitted. Note that in the following description, the transformation function from the supine position MRI image coordinate system to the supine position normalized coordinate system obtained in this processing step is expressed as $\phi_s(x)$. In addition, a transformation function from the supine position normalized coordinate system to the supine position MRI image coordinate system is expressed as $\phi_s^{-1}(x)$.

(Step S380) Deformation of MRI Image

In step S380, the image deformation unit 1060 generates a deformed image by deforming a prone position MRI image to a supine position image based on the processing results obtained in steps S320 and S360. More specifically, the image deformation unit 1060 performs coordinate transformation of a position $x_p$ of each of all the voxels (pixels constituting volume data) constituting the prone position MRI image by the calculation represented by equation (12), thereby calculating a position $x_d$ after transformation.

$$x_d = \phi_s^{-1}[\phi_{ps}\{\phi_p(x_p)\}] \qquad (12)$$

The image deformation unit 1060 then generates volume data having a intensity value $I_p(x_p)$ at the position $x_d$ after transformation. Note that a function $\phi_{ps}(x)$ is an arbitrary transformation function from the prone position normalized coordinate system to the supine position normalized coordinate system, and is an identity function represented by equation (13). In addition, the domain of the transformation function $\phi_{ps}(x)$ is the same rectangular region as that of $\phi_p^{-1}(x)$.

$$X = \phi_{ps}(x) \qquad (13)$$

The volume data generated by the above processing is expressed as a deformed MRI image $I_d(x)$. That is, the deformed MRI image $I_d(x)$ is calculated from the prone position MRI image $I_p(x)$ by the calculation represented by equation (14).

$$I_d(x) = I_p[\phi_p^{-1}\{\phi_{ps}^{-1}(\phi_s(x))\}] \qquad (14)$$

The calculation represented by equation (12) executed in this processing step specifically indicates the following. That is, the position $x_p$ in the prone position MRI image coordinate system is transformed to the prone position normalized coordinate system, and the prone position normalized coordinate system is equated with the supine position normalized coordinate system. The coordinate value is then transformed to the supine position MRI image coordinate system. That is, it is assumed that the difference in shape between the prone position and the supine position is canceled by the respective normalizations (each anatomically identical point is mapped to almost matching coordinates in the normalized coordinate system by normalization). A transformation between the prone position MRI image coordinate system and the supine position MRI image coordinate system is obtained (deformation alignment is performed) based on the above assumption.

The above description has exemplified the case in which an identity function is used as the coordinate transformation $\phi_{ps}(x)$ between the prone position normalized coordinate system and the supine position normalized coordinate system. However, an arbitrary coordinate transformation may be used. For example, $\phi_{ps}(x)$ may be a deformation function which improves the inter-image similarity between a deformed MRI image and a supine position MRI image. For example, $\phi_{ps}(x)$ can be expressed by FFD (Free Form Deformation) which is one of typical techniques for nonlinear coordinate transformation. In this case, the processing of optimizing a deformation parameter of FFD is executed to maximize the inter-image similarity represented by equation (15).

$$E = \sum_{x \in \Omega} \{I_s(x) - I_d(x)\}^2 \qquad (15)$$

Note that $I_s(x)$ represents a supine position MRI image, and $\Omega$ represents a breast region in the supine position MRI image coordinate system. The optimization of a deformation parameter of FFD is implemented by a known nonlinear optimization method such as a maximum grade method. In addition, an inter-image similarity may be calculated by any known inter-image similarity calculation method such as a method using a cross-correlation or mutual information content other than the calculation method represented by equation (15). Using the above method makes it possible to generate a deformation with a high intensity value similarity between the prone position MRI image and the supine position MRI image in addition to shape information of the body surface, pectoralis major muscle surface, and the like of the object depicted in the MRI image. This makes it possible to execute alignment between the prone position MRI image and the supine position MRI image with higher accuracy.

(Step S390) Display of Deformed Image

In step S390, the observation image generation unit 1080 generates an observation image such that the deformed image $I_d(x)$ and the supine position MRI image $I_s(x)$ generated in step S380 are juxtaposed to each other. At this time, the observation image generation unit 1080 can clip images (tomographic images) by cutting the deformed image $I_d(x)$ and the supine position MRI image $I_s(x)$ along arbitrary planes in accordance with user's operations and generate an observation image by juxtaposing the clipped images. Alternatively, the observation image generation unit 1080 may generate an observation image by juxtaposing images obtained by volume rendering of the deformed image $I_d(x)$ and the supine position MRI image $I_s(x)$. The observation image generation unit 1080 may form an observation image by superimposing or combining tomographic images generated from the deformed image $I_d(x)$ and the supine position MRI image $I_s(x)$. The observation image generation unit 1080 then displays the observation image generated by the above processing on the monitor 160.

Processing in the processing apparatus 100 according to the first embodiment is executed by the above method. According to this embodiment, normalization is performed in consideration of biomechanical characteristics concerning the deformation of the breast, it is possible to absorb most of variation in position with the deformation and perform transformation to an anatomically common space. This makes it possible to perform the normalization transformation of mapping the breast of the object imaged in the prone position and that in the supine position to anatomically almost matching spaces. In addition, it is possible to provide a mechanism capable of performing deformation alignment between the breast MRI image of the object imaged in the prone position and that in the supine position by a simple method.

(Modification of First Embodiment) Normalization Space Other than Rectangular Shape The first embodiment has exemplified the case in which the normalization unit 1040 generates a normalization deformation for deforming the breast region 402 shown in FIG. 6A to the rectangular shape shown in FIG. 6B in step S320. However, this is not exhaustive. For example, the breast region in the normalized coordinate system may have a shape other than a rectangular shape. For example, the breast region may have a shape enclosed by an arbitrary geometrical curved surface such as a quadratic curved surface. In addition, the processing apparatus 100 may store a plurality of pieces of predetermined shape information and allows the user to arbitrarily select information from them. In this case, the processing apparatus 100 presents, for example, a prone position MRI image and supine position MRI image to the user by, for example, displaying them on the monitor 160. The user may select appropriate shape information while observing the images. This method enables the adaptive selection of a normalization transformation method in accordance with the characteristics of the breast which can have various shapes for each object, thereby having the effect of being able to perform more accurate alignment.

[Second Embodiment] Curved Slice Display

The first embodiment has exemplified the case in which the image deformation unit 1060 generates a deformed MRI image by deforming a prone position MRI image in the processing in step S380. However, an MRI image to be generated is not limited to this. The second embodiment of the present invention will exemplify a case in which an image deformation unit 1060 generates a prone position normalized image by transforming a prone position MRI image to a prone position normalized coordinate system, and a supine position normalized image by transforming a supine position MRI image to a supine position normalized coordinate system, and displays the images side by side.

Only different points from the first embodiment will be described below. Note that the functional arrangement of a processing apparatus according to this embodiment is the same as that shown in FIG. 1 except for the function of an image deformation unit 1060. The image deformation unit 1060 according to the embodiment generates a prone position normalized image $I_{pd}$ and a supine position normalized image $I_{sd}$. A processing procedure in the processing apparatus according to the embodiment is the same as that shown in FIG. 3 except for the contents of processing in steps S380 and S390. The processing in steps S380 and S390 in the embodiment will be described below.

Figure 7A:
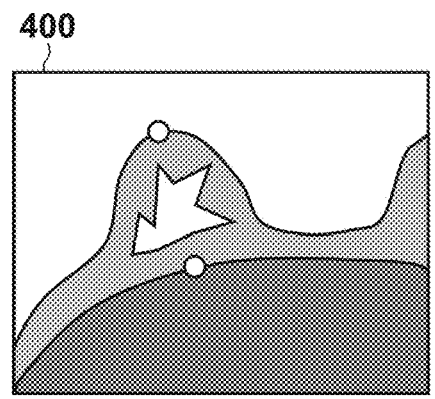
FIG. 7A is a view for explaining image deformation processing according to the first embodiment.
Figure 7B:
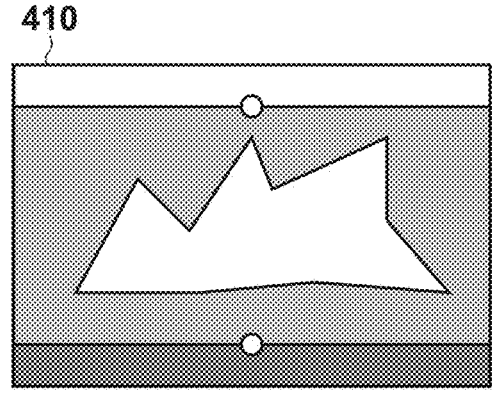
FIG. 7B is a view for explaining image deformation processing according to the first embodiment.
Figure 7C:
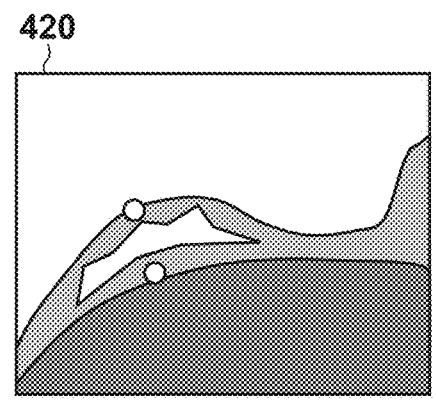
FIG. 7C is a view for explaining image deformation processing according to the first embodiment.
Figure 7D:
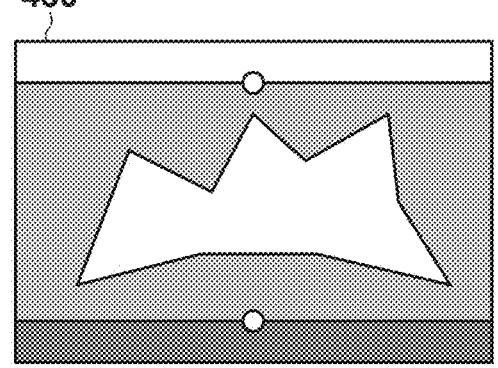
FIG. 7D is a view for explaining image deformation processing according to the first embodiment.

In step S380, the image deformation unit 1060 generates the prone position normalized image $I_{pd}$ by transforming a prone position MRI image $I_p$ to the prone position normalized coordinate system based on a transformation function $\phi_p^{-1}(x)$. FIGS. 7A to 7D are views showing specific examples of images generated by this processing. Referring to FIG. 7A, a prone position MRI image 400 is an example schematically showing the prone position MRI image $I_p$. The image deformation unit 1060 generates a prone position normalized image 410, that is, the prone position normalized image $I_{pd}$, as an image in the prone position normalized coordinate system, as shown in FIG. 7B, by deforming the prone position MRI image 400 based on the transformation function $\phi_p^{-1}(x)$. In step S380, the image deformation unit 1060 performs similar processing for a supine position MRI image $I_s$, and generates a supine position normalized image 430 in FIG. 7D, that is, the supine position normalized image $I_{sd}$, by deforming a supine position MRI image 420 in FIG. 7C based on $\phi_s^{-1}(x)$. With the above processing, the prone position normalized image $I_{pd}$ and the supine position normalized image $I_{sd}$ as three-dimensional volume data are generated.

In step S390, an observation image generation unit 1080 generates an observation image based on the prone position normalized image $I_{pd}$ and the supine position normalized image $I_{sd}$ generated in step S380. More specifically, the observation image generation unit 1080 generates tomographic images $I_{slice,pd}$ and $I_{slice,sd}$ by cutting both the prone position normalized image $I_{pd}$ and the supine position normalized image $I_{sd}$ along x-z planes with y=arbitrary constant, and generates, as an observation image, an image by juxtaposing the tomographic images. In this case, in each of the prone position normalized coordinate system and the supine position normalized coordinate system, the value of a Y-coordinate basically represents the ratio of the distance between the body surface and the pectoralis major muscle surface. Therefore, as the tomographic images $I_{slice,pd}$ and $I_{slice,sd}$, slices (curved slices) on curved surface shapes are cut such that the ratio of the distance between the body surface and the pectoralis major muscle surface in the prone position MRI image coordinate system and that in the supine position MRI image coordinate system becomes constant. This makes it possible to facilitate an advanced comparison between the two images in medical/anatomical terms. For example, this produces the effect of allowing comparative observation of the running of superficial blood vessels existing near the body surface of the breast, the spread of mammary glands in the breast region, and the like throughout a wide range in a single tomographic image.

(Modification of Second Embodiment)

The processing of generating and displaying a curved slice of an MRI image in the above manner need not always be performed for both a prone position MRI image and a supine position MRI image. For example, a processing apparatus 100 may input any one of a prone position MRI image and a supine position MRI image, and may generate and display the above curved slice by executing the processing in steps S300 to S320 in the first embodiment. This method has the effect of allowing advanced image observation of the running of superficial blood vessels, the spread of mammary glands, and the like in medical and anatomical terms.

[Third Embodiment] Statistical Deformation Model Generation and Alignment

A processing apparatus 200 according to this embodiment constructs a model (statistical deformation model) concerning deformation by applying the same normalization processing as that in the first embodiment to many cases (learning cases) and statistically processing the deformations of the respective normalized cases. Normalization between different cases will be described below. At least normal human bodies have almost the same anatomical structure in topological terms regardless of individual differences. In addition, individual differences can be basically absorbed by scale transformation (similarity transformation). With regards to the breasts, however, owing to the development mechanism, the absorption of individual differences by scale transformation described above has its limitation. In contrast, in normal human bodies, the nipples, body surfaces, pectoralis major muscle surfaces, median lines, craniocaudal directions (body axes), and the like are characteristic geometrical structures common to all the individuals in anatomical terms.

The processing apparatus 200 according to this embodiment considers the above characteristics and a space set as a reference space with the characteristic geometrical structures in addition to scale transformation between individuals, and performs coordinate transformation of the breasts of different individual human bodies to the space. This basically absorbs the differences between the individuals and allows transformation to an anatomically common space. The embodiment will exemplify a case in which prone position and supine position MRI images of $N_{samples}$ cases are used as learning cases. In addition, the processing apparatus 200 estimates a deformation by applying a statistical deformation model to an unknown case (target case) different from the learning cases. With this operation, the processing apparatus 200 accurately performs deformation alignment between the prone position and supine position MRI images of the target case.

(Functional Arrangement)

Figure 8:
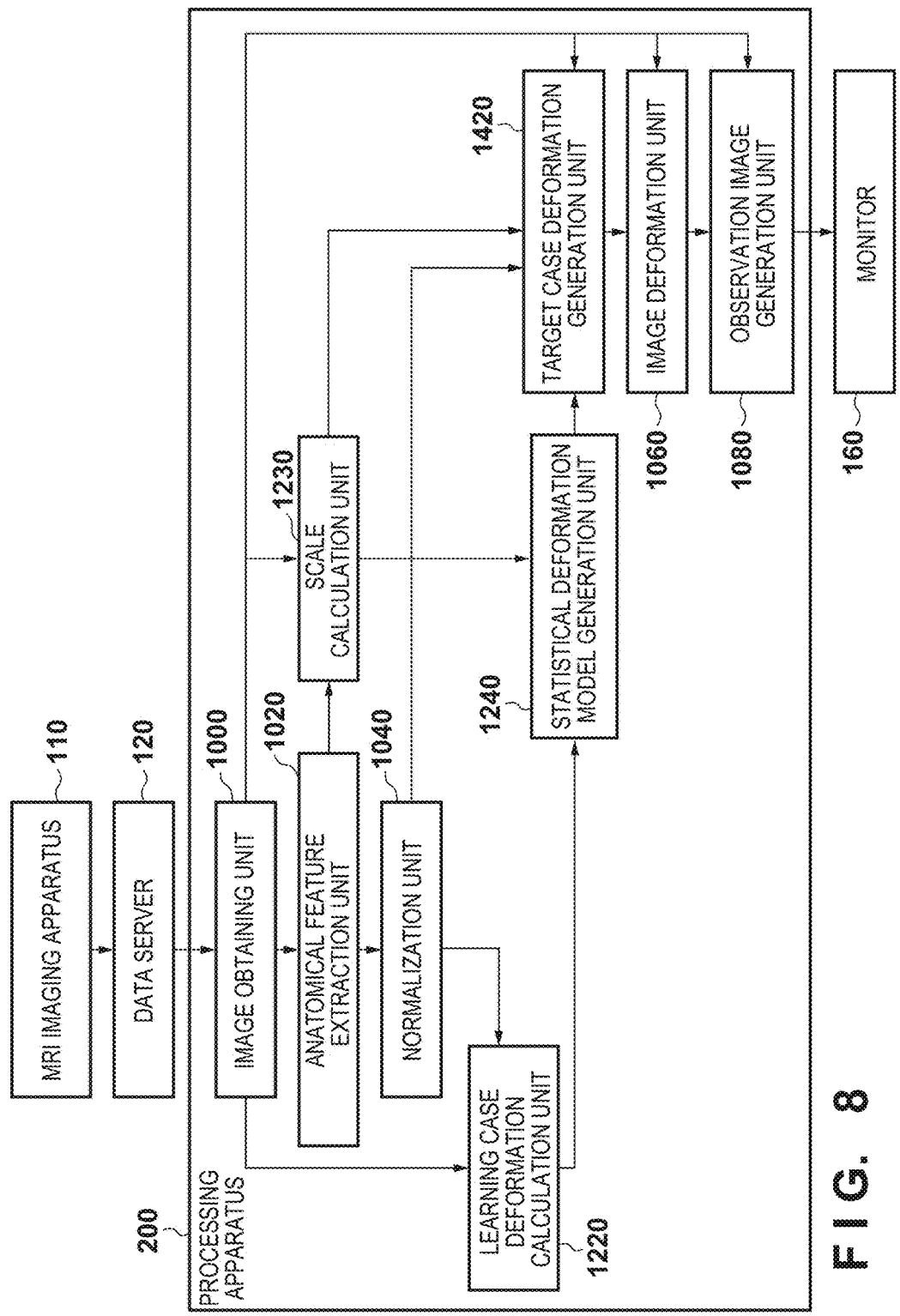
FIG. 8 is a block diagram showing the functional arrangement of a processing system according to the third embodiment.

FIG. 8 is a block diagram showing the arrangement of a processing system according to this embodiment. In the embodiment, the same reference numerals as in FIG. 1 denote constituent elements having the same functions as in the first embodiment, and a description of them will be omitted. As shown in FIG. 8, the processing apparatus 200 according to the embodiment includes an image obtaining unit 1000, an anatomical feature extraction unit 1020, a normalization unit 1040, a learning case deformation generation unit 1220, a scale calculation unit 1230, a statistical deformation model generation unit 1240, a target case deformation generation unit 1420, an image deformation unit 1060, and an observation image generation unit 1080.

The learning case deformation generation unit 1220 generates a deformation from the prone position to the supine position based on an MRI image of each learning case. The scale calculation unit 1230 calculates scales concerning the respective learning cases. The statistical deformation model generation unit 1240 generates a statistical deformation model based on the deformation and scale concerning each learning case. The target case deformation generation unit 1420 generates a deformation from the prone position to the supine position of the target case.

(Processing Procedure)

The overall operation performed by the processing apparatus 200 will be described next. In this embodiment, a CPU 211 executes programs stored in a main memory 212 to implement the functions of the respective units. In addition, the result of each process performed by the processing apparatus 200 to be described below is recorded by being stored in the main memory 212.

Processing performed by the processing apparatus 200 according to this embodiment includes processing in a learning phase and processing in a deformation estimation phase. The processing apparatus 200 executes the processing in the learning phase first, and then executes the processing in the deformation estimation phase. In the processing in the learning phase, the processing apparatus 200 learns deformations between prone position and supine position MRI images of many cases and generates a statistical deformation model. In the processing in the deformation estimation phase, the processing apparatus 200 executes deformation alignment between the prone position and the supine position of the target case by using the statistical deformation model calculated in the learning phase.

Although this embodiment will exemplify a case in which the processing apparatus 200 executes both the processing in the learning phase and the processing in the deformation estimation phase, different processing apparatuses may execute the processing in the learning phase and the processing in the deformation estimation phase. In addition, the processing apparatus 200 according to the embodiment may execute, for example, only the processing in the learning phase instead of executing both the processing in the learning phase and the processing in the deformation estimation phase. In addition, the provision of a statistical deformation model obtained as a result of the processing in the learning phase itself is incorporated in the embodiment.

(Processing in Learning Phase)

Figure 9:
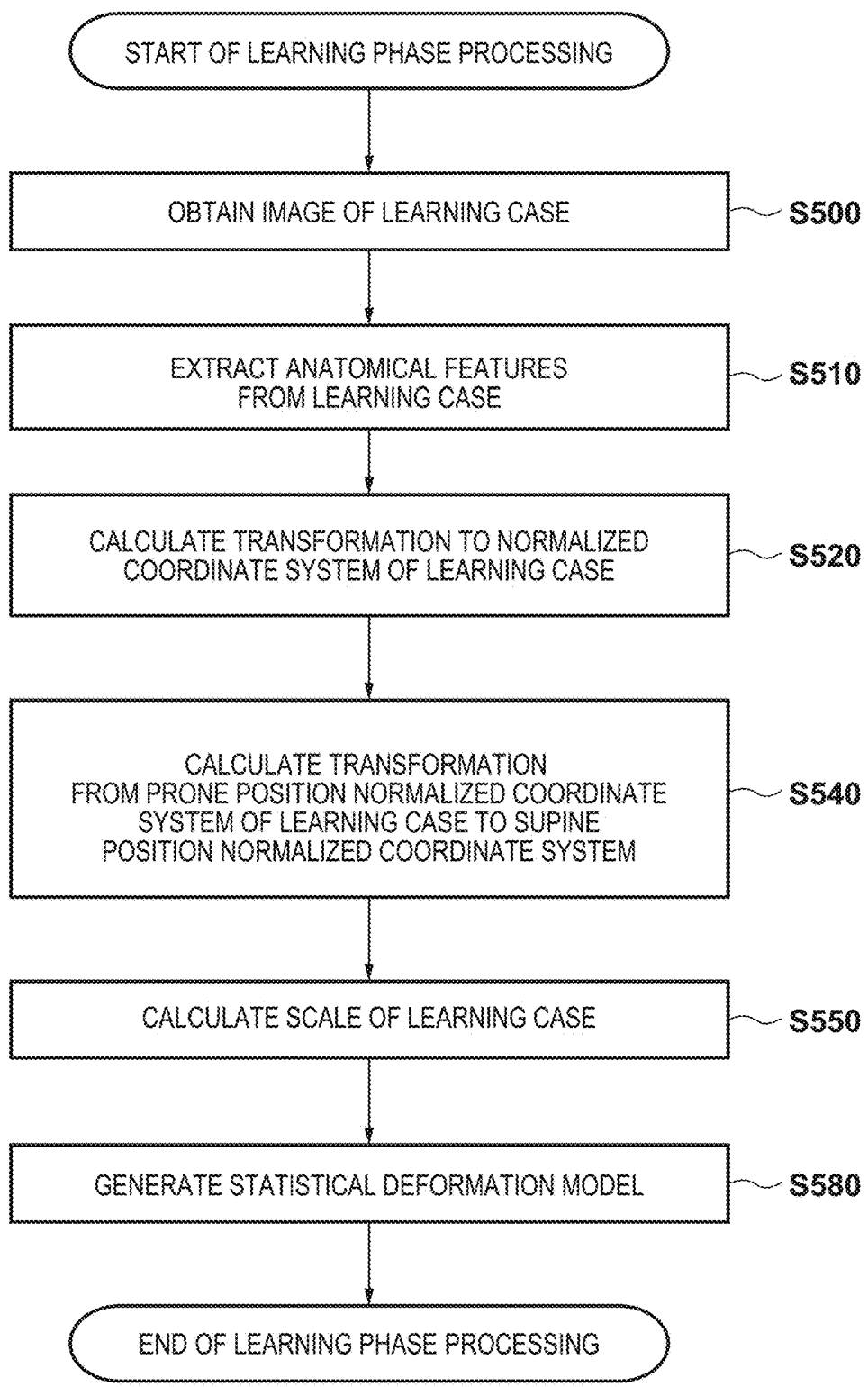
FIG. 9 is a flowchart showing a processing procedure in a learning phase in a processing apparatus according to the third embodiment.

FIG. 9 is a flowchart for explaining a processing procedure in the learning phase which is performed by the processing apparatus 200 according to this embodiment. The processing in the learning phase according to the embodiment will be described in detail below in accordance with the processing procedure shown in this flowchart.

(Step S500) Calculation of Images of Learning Cases

In step S500, the image obtaining unit 1000 obtains prone position MRI images and supine position MRI images of $N_{samples}$ learning cases. This processing can be executed by applying the same processing as that in steps S300 and S340 in the first embodiment to each of the $N_{samples}$ learning cases. A detailed description of the processing will be omitted.

(Step S510) Extraction of Anatomical Features of Learning Cases

In step S510, the anatomical feature extraction unit 1020 extracts anatomical features by processing the prone position MRI images and the supine position MRI images of the learning cases obtained in step S500. This processing can be executed by applying the same processing as that in steps S310 and S350 in the first embodiment to each of the $N_{samples}$ learning cases. A detailed description of the processing will be omitted.

(Step S520) Calculation of Deformation Function of Learning Case to Normalized Coordinate System.

In step S520, the normalization unit 1040 derives a normalization transformation for transforming the shape of the object to a reference shape concerning each learning case based on the anatomical features of each learning case extracted in step S510. More specifically, the normalization unit 1040 calculates a deformation function from the prone position MRI image coordinate system to the prone position normalized coordinate system based on each prone position MRI image. In addition, the normalization unit 1040 calculates a deformation function from the supine position MRI image coordinate system to the supine position normalized coordinate system based on each supine position MRI image. These processes can be executed by the same processing as that in steps S320 and S360 described in the first embodiment. A detailed description of the processes will be omitted.

The deformation function from the prone position MRI image coordinate system to the prone position normalized coordinate system of each learning case calculated by the above processing is expressed as $\phi_{p,j}(x)$. In addition, the deformation function from the supine position MRI image coordinate system to the supine position normalized coordinate system is expressed as $\phi_{s,j}(x)$. In this case, j represents the case number of a learning case, and is defined by $1 \leq j \leq N_{samples}$. That is, the processing of obtaining a deformation function concerning each of the $N_{samples}$ learning cases is executed.

(Step S540) Calculation of Transformation Function from Prone Position Normalized Coordinate System to Supine Position Normalized Coordinate System of Each Learning Case In step S540, the learning case deformation generation unit 1220 calculates a transformation function from the prone position normalized coordinate system to the supine position normalized coordinate system concerning each learning case. More specifically, the learning case deformation generation unit 1220 executes the following processing for each of $N_{samples}$ learning cases.

First of all, the learning case deformation generation unit 1220 obtains corresponding positions in the prone position MRI image coordinate system and the supine position MRI image coordinate system by a user input operation using a mouse 170 and a keyboard 180. Assume that in this case, the corresponding positions are input by the user. The input corresponding positions in the prone position MRI image coordinate system and the supine position MRI image coordinate system are respectively represented by $x_{p,corres,k}$ and $x_{s,corres,k}$. Note that k represents an index of a corresponding point, and is defined by $1 \leq k \leq N_{corres}$ where $N_{corres}$ is the number of corresponding positions. In this case, corresponding positions correspond to, for example, a branching point of blood vessels, a region of the mammary glands which has a characteristic structure or the like in an MRI image, and are a set of positions which can be made to correspond to each other visually by the user.

The learning case deformation generation unit 1220 then transforms the obtained positions $x_{p,corres,k}$ and $x_{s,corres,k}$ by using the transformations to the normalized coordinate systems obtained in step S520. More specifically, the learning case deformation generation unit 1220 executes the processing represented by equation (16) to calculate positions $x'_{p,corres,k}$ and $x'_{s,corres,k}$ in the prone position normalized coordinate system and the supine position normalized coordinate system.

$$x'_{p,corres,k} = \phi_{p,j}(x_{p,corres,k}) (1 \leq k \leq N_{corres}) \quad (16)$$

$$x'_{s,corres,k} = \phi_{s,j}(x_{s,corres,k}) (1 \leq k \leq N_{corres}) \quad (17)$$

In addition, in this processing step, the learning case deformation generation unit 1220 calculates a transformation function $\phi_{ps,j}(x)$ from the prone position normalized coordinate system to the supine position normalized coordinate system based on the calculated positions $x'_{p,corres,k}$ and $x'_{s,corres,k}$. More specifically, the learning case deformation generation unit 1220 calculates the transformation function $\phi_{ps,j}(x)$ so as to approximate the relation represented by equation (18) with the minimum error.

$$x'_{s,corres,k} = \phi_{ps,j}(x'_{p,corres,k}) (1 \leq k \leq N_{corres}) \quad (18)$$

Note that as an error of equation (18), it is possible to use, for example, a square sum error concerning $N_{corres}$ corresponding positions. In this case, the transformation function $\phi_{ps,j}(x)$ is a continuous function defined in the prone position normalized coordinate system. More specifically, the function $\phi_{ps,j}(x)$ can be expressed by using FFD (Free Form Deformation), RBF (Radial Basis Function), or the like.

At this time, the learning case deformation generation unit 1220 is preferably provided with a predetermined constraint such that the value of the transformation function $\phi_{ps,j}(x)$ at a position (a plane with y=0 in this embodiment) on the body surface in the prone position normalized coordinate system outputs a position (likewise a plane with y=0) on the body surface in the supine position normalized coordinate system. Likewise, the learning case deformation generation unit 1220 is preferably provided with a predetermined constraint such that the value of the transformation function $\phi_{ps,j}(x)$ at a position (a plane with y=100 in this embodiment) on the pectoralis major muscle surface in the prone position normalized coordinate system outputs a position (likewise a plane with y=100) on the pectoralis major muscle surface in the supine position normalized coordinate system. With this operation, the learning case deformation generation unit 1220 can obtain transformation functions in consideration of both a condition that the body surfaces and the pectoralis major muscle surfaces match each other and information about corresponding positions inside the breast which are input by the user, in the positional relationship between the prone position and the supine position. In this processing step, the learning case deformation generation unit 1220 executes the above processing for each of the $N_{samples}$ learning cases, and calculates the transformation function $\phi_{ps,j}(x)$ from the prone position normalized coordinate system to the supine position normalized coordinate system for each case.

The above description has exemplified the case in which the learning case deformation generation unit 1220 obtains information about corresponding positions in the prone position MRI image coordinate system and the supine position MRI image coordinate system, and calculates the deformation function $\phi_{ps,j}(x)$ based on the obtained information. However, a method of calculating the deformation function $\phi_{ps,j}(x)$ is not limited to this example. For example, as in the same manner as described in the processing in step S380 in the first embodiment, the learning case deformation generation unit 1220 may calculate the deformation function $\phi_{ps,j}(x)$ based on the inter-image similarity between a prone position MRI image and a supine position MRI image. In addition, the learning case deformation generation unit 1220 may calculate the deformation function $\phi_{ps,j}(x)$ based on the inter-image similarity between a prone position MRI image and a supine position MRI image in addition to information of corresponding positions in the prone position MRI image coordinate system and the supine position MRI image coordinate system. The above method has the effect of being able to obtain a deformation of each learning case more accurately.

(Step S550) Calculation of Scale of Learning Case

In step S550, the scale calculation unit 1230 calculates a scale of each learning case. In this case, a scale of a case is a numerical value representing the size of a breast region which differs for each case. A scale is calculated by, for example, measuring the value of the distance between the nipple position of an object in the prone position and a body surface position on a median line which is nearest to the nipple position. The user may perform this processing by inputting, to the processing apparatus 200, a numerical value directly measured with respect to the object in the prone position by using a measurement instrument. Alternatively, the processing apparatus 200 may be configured to measure the value of the distance on a prone position MRI image. In this case, the processing apparatus 200 may calculate the above measurement value by automatically processing a prone position MRI image. Alternatively, the processing apparatus 200 may be configured to present a prone position MRI image to the user by using a monitor 160 or the like and obtain a measurement value by the operations of the mouse 170 and the keyboard 180 by the user. For example, the processing apparatus 200 displays a prone position MRI image on the monitor 160, makes the user designate a nipple position of an object depicted on the image and a body surface position on a median line nearest to the nipple position, and calculates the distance between the positions, thereby implementing the above processing.

The above description has exemplified the method of calculating a scale of a case by using the distance (Euclidean distance) between the nipple position and the body surface position on a median line nearest to the nipple position. However, a scale calculation method to be used is not limited to this method. For example, a scale may be calculated by using the geodesic distance between the above two points. This has the effect of being able to calculate a scale value in consideration of also the difference in shape between the breasts of the respective cases. In addition, a scale may be calculated based on, for example, the volume of a breast region, the distance to an outer end of the breast, the chest circumference of the object, in addition to the distance or geodesic distance between the above two points. Furthermore, a method of calculating a scale is not limited to one method. For example, a scale may be calculated based on values calculated by a plurality of types of methods. In this case, the values calculated by a plurality of types of methods may be vectorized into a multidimensional scale value. Alternatively, a scale value may be calculated as a scalar value by performing an averaging operation or linear combination operation of values calculated by a plurality of types of methods. In any case, it is preferable to calculate scales using the same method and reference with respect to $N_{samples}$ cases.

A scale calculated by the above method is expressed as $v_j$ ($1 \le j \le N_{samples}$). In this embodiment, a scale value is the ratio between a scalar value, which is the distance (Euclidean distance) between the nipple position in the prone position and the body surface position on a median line nearest to the nipple position, and a predetermined reference value. In this case, the predetermined reference value is, for example, the value of the distance from a nipple position on the standard breast and a body surface position on a median line nearest to the nipple position.

(Step S580) Generation of Statistical Deformation Model

Figure 10:
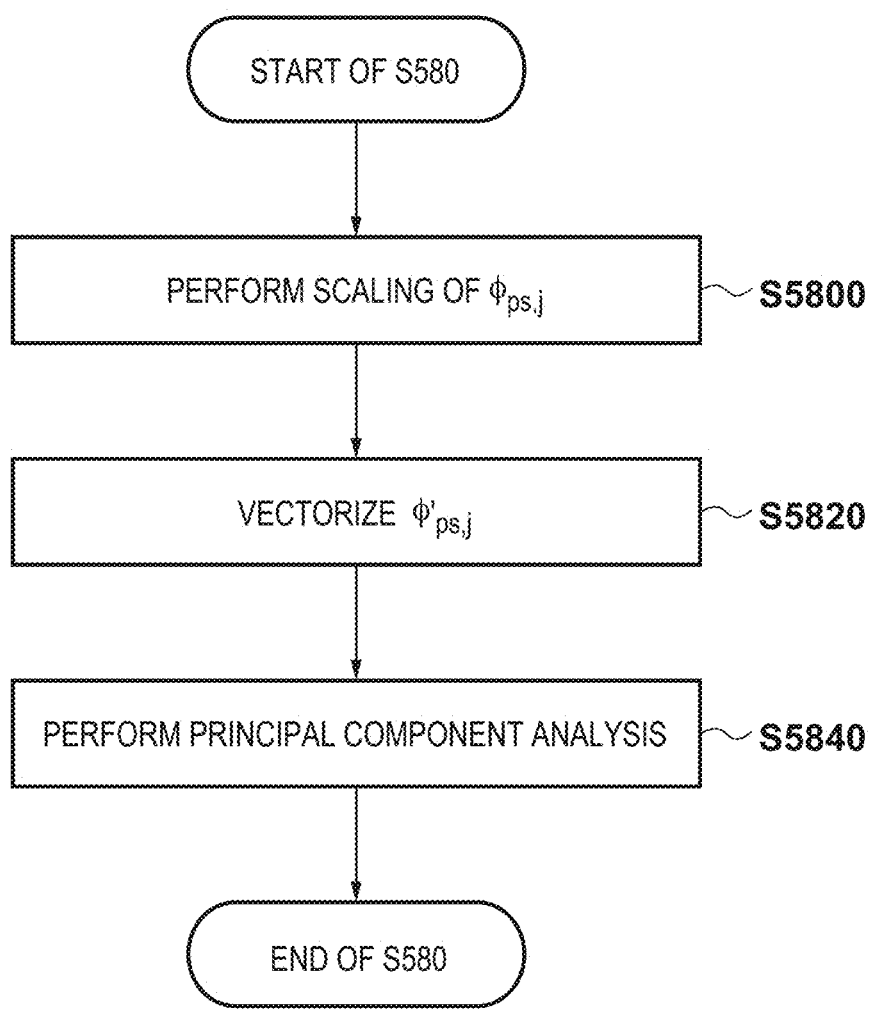
FIG. 10 is a flowchart showing a processing procedure in step S580 in the processing apparatus according to the third embodiment.

In step S580, the statistical deformation model generation unit 1240 generates a statistical deformation model based on $\phi_{ps,j}(x)$ and $v_j$ concerning $N_{samples}$ cases which are calculated by the processing in steps S500 to S570. FIG. 10 is a flowchart for explaining the processing in step S580 in more detail. This processing will be described along the flowchart of FIG. 10.

<Step S5800> Scaling of $\phi_{ps,j}(x)$

In step S5800, the statistical deformation model generation unit 1240 calculates a transformation function $\phi'_{ps,j}(x)$ by scaling the transformation function $\phi_{ps,j}(x)$ based on the transformation function $\phi_{ps,j}(x)$ and the scale $v_j$ concerning the $N_{samples}$ cases. More specifically, the statistical deformation model generation unit 1240 calculates the transformation function $\phi'_{ps,j}(x)$ according to equation (19).

$$\phi'_{ps,j}(x') = \phi_{ps,j}(x)/v_j \tag{19}$$

In this case, however, when $x=(x, y, z)^T$, $x'=(xXv_j, y, zXv_j)^T$. That is, $\phi'_{ps,j}(x)$ is a function obtained by scaling $\phi_{ps,j}(x)$ with the scale value $v_j$ of the case with respect to X-coordinates and Z-coordinates. Note that the domain of $\phi'_{ps,j}(x)$ is smaller than that of $\phi_{ps,j}(x)$ by the scale value $v_j$ of the case with respect to x-coordinates and z-coordinates. The statistical deformation model generation unit 1240 executes the above processing for the transformation functions $\phi_{ps,j}(x)$ ($1 \le j \le N_{samples}$) for all the $N_{samples}$ cases, and calculates the transformation functions $\phi'_{ps,j}(x)$ ($1 \le j \le N_{samples}$) by scaling the respective cases.

<Step S5820> Vectorization of $\phi'_{ps,j}(x)$

In step S5820, the statistical deformation model generation unit 1240 discretizes the transformation functions $\phi'_{ps,j}(x)$ after scaling which is calculated in step S5800. This discretization processing is executed by the following procedure.

First of all, the statistical deformation model generation unit 1240 obtains a domain common to the transformation functions $\phi'_{ps,j}(x)$ concerning the $N_{samples}$ cases. The $N_{samples}$ transformation functions $\phi'_{ps,j}(x)$ respectively have different domains depending on the shapes of the body surfaces and pectoralis major muscle surfaces, scale values, and the like of the respective cases. Assume that in this embodiment, a domain in which $\phi'_{ps,j}(x)$ is defined is common to all the $N_{samples}$ cases. In this domain, therefore, all the $N_{samples}$ transformation functions $\phi'_{ps,j}(x)$ have values.

The statistical deformation model generation unit 1240 then samples the values of the transformation functions $\phi'_{ps,j}(x)$ over the common domain described above, and generates discretized vectors by vertically arranging the sampling results. In this case, the statistical deformation model generation unit 1240 generates discretized vectors by sequentially arranging values sampled in a raster scan form at predetermined intervals within the above domain so as to form vectors. Note that the transformation function $\phi'_{ps,j}(x)$ is a function for returning three-dimensional values of x, y, and z, and hence the statistical deformation model generation unit 1240 generates a discretized vector for each coordinate axis. In this case, discretized vectors along the three-dimensional coordinate axes x, y, and z are respectively represented by $p_{x,j}$, $p_{y,j}$, and $p_{z,j}$. A discretized vector is a real vector having a dimension corresponding to the number of times of sampling by the above raster scan scheme.

The statistical deformation model generation unit 1240 applies the above processing to the $N_{samples}$ transformation functions $\phi'_{ps,j}(x)$. With this operation, the statistical deformation model generation unit 1240 obtains $N_{samples}$ discretized vectors $p_{x,j}$, $p_{y,j}$, and $p_{z,j}$. Note that the discretized vectors obtained by sampling in the raster scan form described above can be inversely transformed to transformation functions in the real space by using an arbitrary interpolation function and the like. Assume that in this embodiment, $\phi'_{ps,j}(x)$ is approximated by an interpolation function $f_{interp}$ ($p_{x,j}$, $p_{y,j}$, $p_{z,j}$, x) having, as arguments, the discretized vectors $p_{x,j}$, $p_{y,j}$, and $p_{z,j}$ and a position x in the real space.

<Step S5840> Generation of Statistical Deformation Model by Principal Component Analysis In step S5840, the statistical deformation model generation unit 1240 generates a statistical deformation model by performing principal component analysis of the discretized vectors $p_{x,j}$, $p_{y,j}$, and $p_{z,j}$ ($1 \le j \le N_{samples}$) calculated in step S5820. Since principal component analysis can be executed by a known method, a detailed description will be omitted. As a result of the principal component analysis, the statistical deformation model generation unit 1240 obtains average vectors $e_{ave,x}$, $e_{ave,y}$, and $e_{ave,z}$ concerning the respective discretized vectors and eigenvectors $e_{x,k}$, $e_{y,k}$, and $e_{z,k}$ ($1 \le k \le N_{mode}$), where $N_{mode}$ is the total number of eigenvectors calculated by principal component analysis, and can be set by, for example, setting a predetermined threshold with respect to a cumulative contribution ratio calculated by principal component analysis. In this embodiment, the average vectors and the eigenvectors calculated by the above processing will be referred to as statistical deformation models.

Note that the average vectors and the eigenvectors can approximate discretized vectors by calculating equation (20) which calculates the linear sum of these vectors with appropriate weights.

$$P_{x,j} \cong e_{ave,x} + \sum_{xk=1}^{N_{mode}} b_k e_{x,k} = e_{ave,x} + E_x b \tag{20}$$

where $E_x$ is a matrix of the vectors $e_{x,k}$ arranged laterally, and b is a vector obtained by arranging $b_k$ longitudinally, which is called a factor vector in this embodiment. It has already been known that, in general, when a case count $N_{samples}$ is sufficiently large, discretized vectors representing their deformations can be accurately approximated by the linear sum of eigenvectors and average vectors smaller in number than $N_{samples}$.

Processing in the learning phase in this embodiment is executed by the processing in steps S500 to S580 described above. As a result of this processing, a statistical deformation model is generated.

(Processing in Deformation Estimation Phase)

Figure 11:
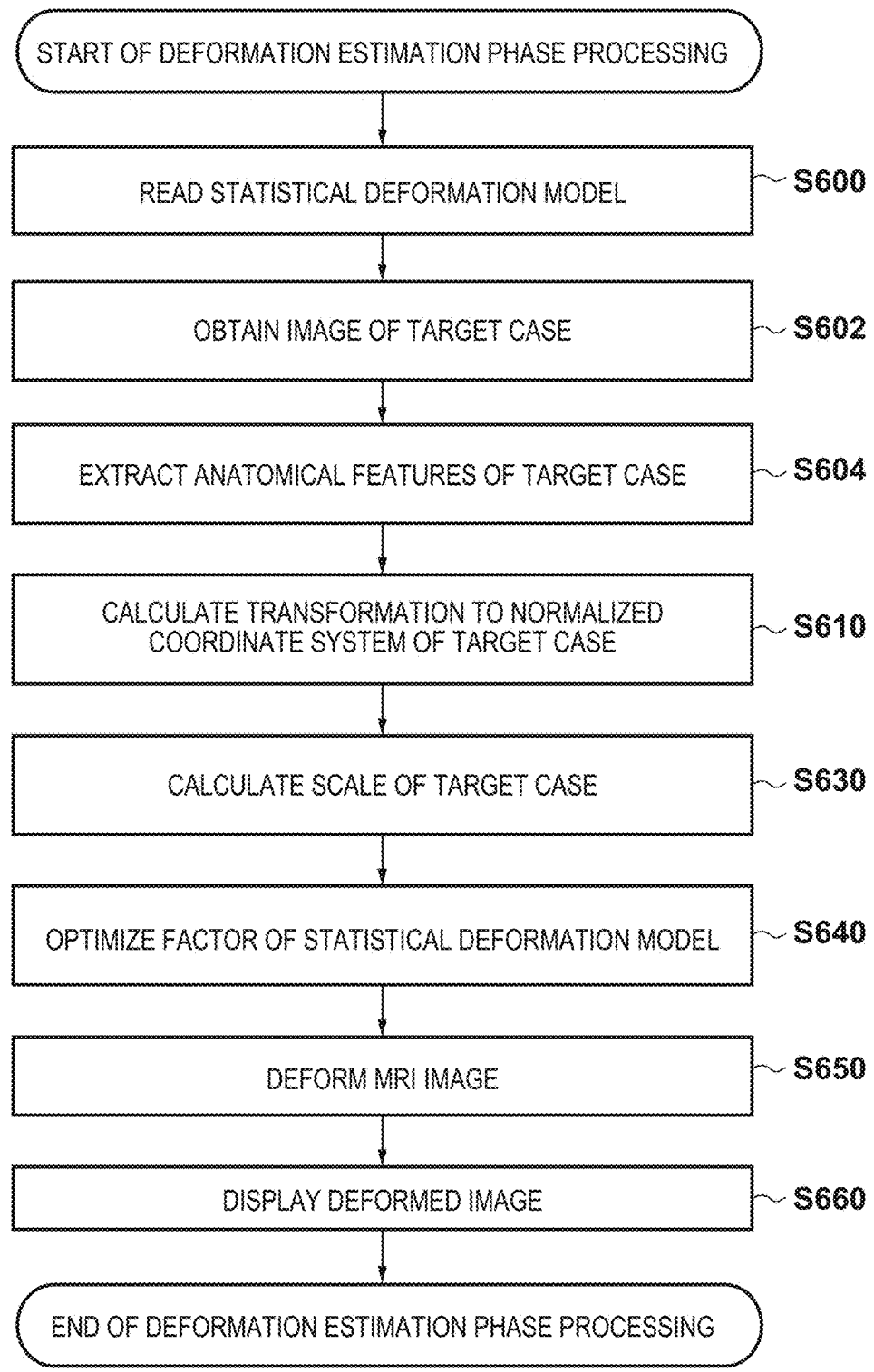
FIG. 11 is a flowchart showing a processing procedure in a deformation estimation phase in the processing apparatus according to the third embodiment.

FIG. 11 is a flowchart for explaining a processing procedure in the deformation estimation phase performed by the processing apparatus 200 according to this embodiment. The processing in the deformation estimation phase according to this embodiment will be described in detail below in accordance with the processing procedure shown in this flowchart.

(Step S600) Reading of Statistical Deformation Model

In step S600, the processing apparatus 200 reads out the statistical deformation model generated by the processing in the learning phase to the main memory 212 of the processing apparatus 200.

(Step S602) Obtaining of Image of Target Case

In step S602, the image obtaining unit 1000 obtains prone position and supine position MRI images of the target case. This processing can be executed in the same manner as the processing in steps S300 and S340 in the first embodiment. A detailed description of this processing will be omitted.

(Step S604) Extraction of Anatomical Features of Target Case

In step S604, the anatomical feature extraction unit 1020 extracts anatomical features from the target case by processing the prone position and supine position MRI images of the target case obtained in step S602. This processing can be executed in the same manner as the processing in steps S310 and S350 in the first embodiment. A detailed description of the processing will be omitted.

(Step S610) Calculation of Transformation to Normalized Coordinate System of Target Case In step S610, the normalization unit 1040 calculates a transformation from the prone position MRI image coordinate system of the target case to the prone position normalized coordinate system and a transformation from the supine position MRI image coordinate system to the supine position normalized coordinate system based on the anatomical features of the target case extracted in step S604. The normalization unit 1040 executes this processing by applying the same processing as the processing in step S520, which has been described as the processing in the learning phase, to the target case. A detailed description of the processing will be omitted. A transformation from the prone position MRI image coordinate system to the prone position normalized coordinate system which is calculated by this processing is expressed as $\phi_{p,target}(x)$. In addition, a transformation from the supine position MRI image coordinate system to the supine position normalized coordinate system is expressed as $\phi_{s,target}(x)$.

(Step S630) Calculation of Scale of Target Case

In step S600, the scale calculation unit 1230 calculates a scale of the target case. The scale calculation unit 1230 executes this processing by applying the same processing as that in step S550, which has been described as the processing in the learning phase, to the target case. A detailed description of the processing will be omitted. The scale of the target case calculated by this processing is expressed as $v_{target}$.

(Step S640) Optimization of Factor of Statistical Deformation Model

In step S600, the target case deformation generation unit 1420 calculates a transformation between the prone position MRI image coordinate system and the supine position MRI image coordinate system of the target case. That is, the target case deformation generation unit 1420 executes deformation alignment processing between the prone position MRI image and the supine position MRI image. The target case deformation generation unit 1420 executes this processing based on the statistical deformation model obtained by the processing in the learning phase and the prone position and supine position MRI images of the target case. More specifically, the target case deformation generation unit 1420 calculates a factor vector b which maximizes an evaluation function G(b) calculated by the calculation represented by equation (21).

$$G(b)=G_{simil}\{D(I_p,b),I_s\} \tag{21}$$

where $I_p$ is the prone position MRI image of the target case, and $I_s$ is the supine position MRI image of the target case. In addition, a function $G_{simil}(I_1, I_2)$ is a function for evaluating the similarity between two images, which is provided as an argument, and can be implemented by a known inter-image similarity evaluation method such as an SSD, SAD, cross-correlation, or mutual information content method.

In addition, a function D(I, b) is a function for deforming an image I based on the factor vector b of the statistical deformation model. More specifically, the function D(I, b) performs the following processing. That is, this function calculates discretized vectors $p_x$, $p_y$, and $p_z$ by the calculation represented by expressions (22) based on the factor vector b.

$$p_x \cong e_{ave,x}+E_x b$$

$$p_y \cong e_{ave,y}+E_y b$$

$$p_z \cong e_{ave,z}+E_z b \tag{22}$$

The target case deformation generation unit 1420 obtains a deformation function $\phi_{target}(X)$ by equation (23) based on the calculated discretized vectors $p_x$, $p_y$, and $p_z$.

$$\phi_{target}(x)=\phi_s^{-1}[f_{interp}\{p_x,p_y,p_z,\phi_p(x)\}] \tag{23}$$

The statistical deformation model generation unit 1240 further calculates a transformation function $\phi'_{target}(x)$ by scaling the transformation function $\phi_{target}(x)$ by using the scale $v_{target}$ of the target case calculated in step S630 according to equation (24).

$$\phi'_{target}(x)=\phi_{target}(x) \times v_{target} \tag{24}$$

In this case, if $x=(x, y, z)^T$, $x=(xXv_{target}, y, zXv_{target})^T$. That is, $\phi'_{target}(x)$ is a function obtained by scaling $\phi_{target}(x)$ concerning X-coordinates and Z-coordinates with a scale value $v_j$ of the target case, and further scaling the value of the function with a scale value $v_{target}$.

The function D(I, b) then deforms the image I based on the deformation function $\phi'_{target}(x)$. That is, D($I_p$, b) in equation (21) performs the calculation represented by equation (25) given below.

$$D(I_p,b)=I_p\{\phi'_{target}(x)\} \tag{25}$$

As described above, the evaluation function G(b) represented by equation (21) evaluates the similarity between the image obtained by deforming the prone position MRI image and the supine position MRI image based on the factor vector b. In this processing step, the target case deformation generation unit 1420 calculates the factor vector b which maximizes the value of the evaluation function represented by equation (21) by using a nonlinear optimization method such as a steepest descent method, quasi-Newton's method, or conjugate gradient method. The factor vector obtained by this processing is expressed as $b_{opt}$.

The above description has exemplified the case in which a factor vector is calculated based on the inter-image similarity between a deformed MRI image obtained by deforming a prone position MRI image and a supine position MRI image. However, a factor vector calculation method to be used is not limited to this. If, for example, it is possible to identify corresponding positions between a prone position MRI image and a supine position MRI image of a target case, the processing apparatus 200 may obtain these pieces of position information, and the target case deformation generation unit 1420 may calculate a factor vector so as to approximate the correspondence relationship between them. When, for example, the processing apparatus 200 obtains these corresponding positions by a user input, it is possible to estimate a deformation so as to match the positions which the user wants to match between the two images.

In addition, it is possible to generate a new evaluation function by adding an evaluation function for the error between corresponding positions between a prone position MRI image and a supine position MRI image of the target case to the inter-image similarity evaluation function represented by equation (21). This function has the effect of being able to perform deformation estimation with higher accuracy based on both information concerning an inter-image similarity and information concerning corresponding positions input by the user. Note that the information concerning the corresponding positions is not limited to information input by the user, and may be automatically obtained from both a prone position MRI image and a supine position MRI image by using, for example, a feature point detection/feature point association method such as nSIFT. This makes it possible to execute deformation estimation more efficiently.

In addition, a factor vector to be calculated in this processing step need not always be obtained by, for example, maximizing an evaluation function. For example, a factor vector may be a 0 vector. In this case, the deformation calculated in this processing step is the average deformation calculated in step S580 as processing in the learning phase in this embodiment. It is possible to execute deformation estimation with higher accuracy than deformation estimation using $\phi_{ps}(x)$ as an identity function in the first embodiment described above.

(Step S650) Deformation of MRI Image

In step S600, the image deformation unit 1060 generates a deformed MRI image by deforming the prone position MRI image based on the transformation calculated in step S640. More specifically, the image deformation unit 1060 calculates a deformed MRI image $I_d$ by deforming a prone position MRI image $I_p$ of the target case by using the image deformation function D(I, b) represented by equation (24) based on a factor vector $b_{opt}$.

(Step S660) Display of Deformed Image

In step S600, the observation image generation unit 1080 generates an observation image having the deformed MRI image $I_d$, generated in step S650, and the supine position MRI image of the target case juxtaposed. Specific processing in this processing step is the same as that in step S390 in the first embodiment, and hence a detailed description of the processing will be omitted.

With the processing in steps S600 to S660 described above, the processing in the deformation estimation phase in this embodiment is executed. As a result of this processing, deformation estimation processing is executed between the prone position MRI image and the supine position MRI image of the target case. A deformed MRI image is generated by deforming the prone position MRI image so as to correspond to the supine position MRI image and is displayed together with the supine position MRI image, thereby presenting an input image in a form that allows easy comparison.

(First Modification of Third Embodiment) Normalization to Standard Shape (Including Bowl-Like Shape and Circular Cone) Including Different Normalizations Between Prone Position and Supine Position This embodiment has exemplified the case in which in the processing in steps S540 and S610, the transformations $\phi_p$ and $\phi_s$ to normalized coordinate systems are calculated based on the distances and azimuths from the nipple position as a reference point to point groups constituting the body surface and the pectoralis major muscle surface. However, a method of calculating the transformations $\phi_p$ and $\phi_s$ is not limited to this example. For example, the transformations $\phi_p$ and $\phi_s$ to the normalized coordinate systems in steps S540 and S610 can be transformation functions to standard shapes concerning the prone position and the supine position. In this case, a standard shape can be a breast shape of a specific case.

More specifically, the user can arbitrarily select one of $N_{samples}$ cases learned in this embodiment, and the body surface shape and pectoralis major muscle shape of the selected case can be standard shapes. Alternatively, a standard shape may be an average shape of $N_{samples}$ cases to be learned. In addition, a standard shape is not necessarily selected from learning cases, and the body surface shape and pectoralis major muscle shape of a case different from learning cases may be used. Furthermore, a standard shape is not limited to the shape of an existing specific case, and may be a simulated shape of an artificial breast. For example, it is possible to use, as a standard shape, the shape obtained by cutting a sphere or elliptical body, a shape like a circular cone or bowl-like shape, or the like. In addition, the same shape in the prone position and the supine position may be used as a standard shape, or different shapes in the prone position and the supine position may be used as standard shapes. Alternatively, the processing apparatus 200 may have information concerning a plurality of predetermined standard shapes, and may select an appropriate standard shape based on the anatomical features of a learning case. In any case, the statistical deformation model in this embodiment is a model approximately expressing a transformation function between a coordinate system with reference to a standard shape in the prone position and a coordinate system with reference to a standard shape in the supine position.

(Second Modification of Third Embodiment) Case in which Deformation to Normalized Coordinate System of Learning Case May be FFD; in this Case, SDM May be Used as Statistical Model This embodiment has exemplified the case in which in the processing in step S580, the deformation $\phi_{ps,j}(x)$ calculated in step S540 is expanded as a deformation field (discretized vector) in the space of the normalized coordinate system. However, this expansion may be performed in another form. For example, in step S540, the deformation $\phi_{ps,j}(x)$ may be expressed by FFD, and the discretized vectors $p_{x,j}$, $p_{y,j}$, and $p_{z,j}$ may be calculated by vectorization of a parameter (a control amount of a control point) of FFD. In this case, a statistical deformation model can be constructed by the method (Statistical Deformation Model method) disclosed in NPL 2. This method obviates the necessity to expand the deformation $\phi_{ps,j}(x)$ to a discretized vector in a deformation field in step S580, and has the effect of being able to reduce a calculation processing amount and the consumption of memory capacity.

[Fourth Embodiment] Example of Constructing Statistical Atlas of Breast in Prone Position A processing apparatus 800 according to this embodiment uses MRI images obtained by imaging the breasts of many cases in the prone position as learning data, and normalizes the shapes of the breasts, which differ among the respective cases, thereby constructing a statistical shape model efficiently expressing the shapes of the breasts. Although this embodiment will exemplify a case in which data obtained by imaging the breast in the prone position is used as learning data in the embodiment, data obtained by imaging the breast in other postures may be used. For example, the postures may be the supine position, the upright position, and the like.

(Functional Arrangement)

Figure 12:
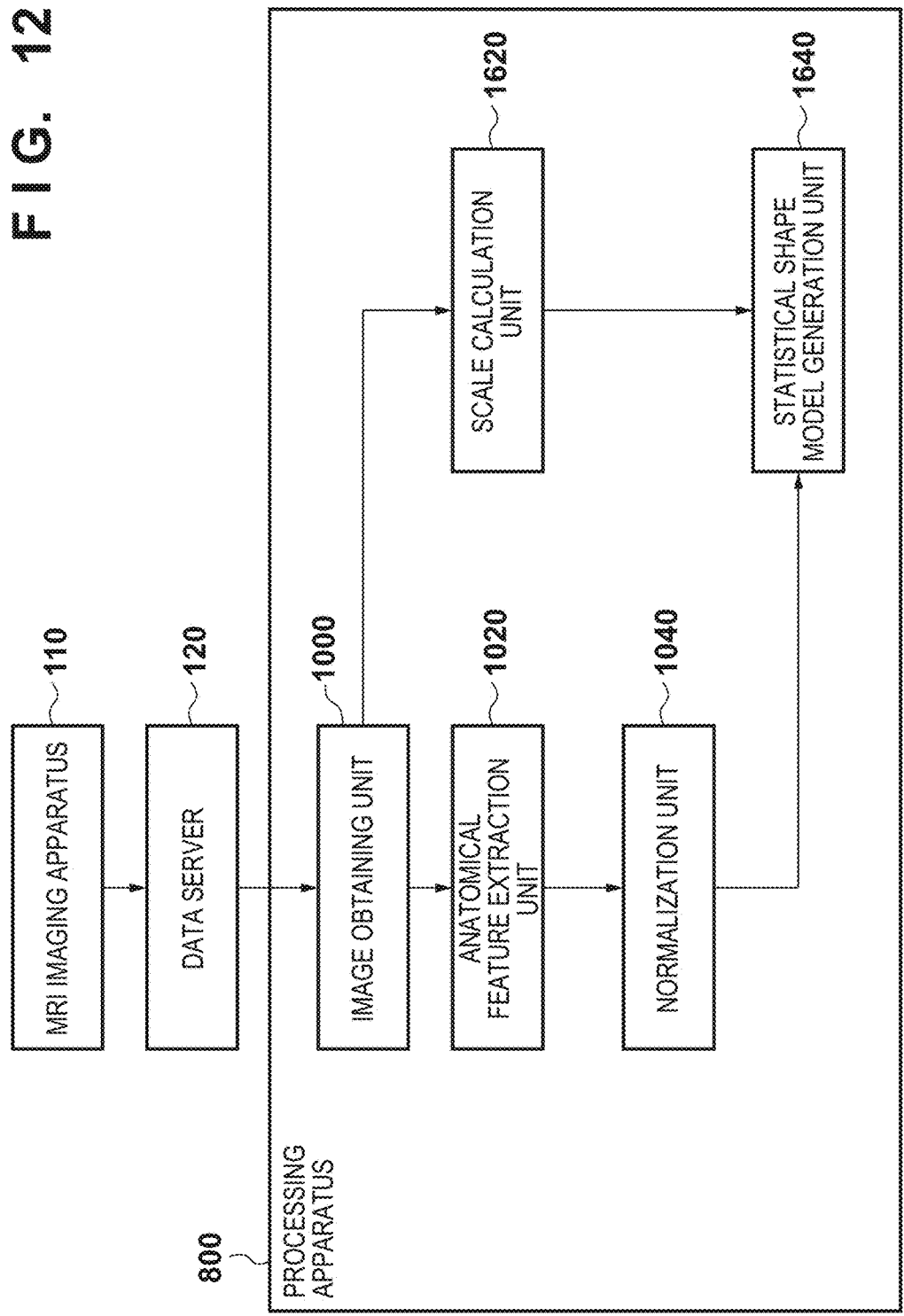
FIG. 12 is a block diagram showing the functional arrangement of a processing system according to the fourth embodiment.

FIG. 12 is a block diagram showing the arrangement of a processing system according to this embodiment. In the embodiment, the same reference numerals as in FIG. 1 denote constituent elements having the same functions as in the first embodiment, and a description of them will be omitted. As shown in FIG. 12, the processing apparatus 800 according to this embodiment includes an image obtaining unit 1000, an anatomical feature extraction unit 1020, a normalization unit 1040, a scale calculation unit 1620, and a statistical shape model generation unit 1640. The scale calculation unit 1620 calculates a scale concerning each learning scale. The statistical shape model generation unit 1640 generates a statistical shape model based on a deformation/scale concerning each learning case.

(Processing Procedure)

Figure 13:
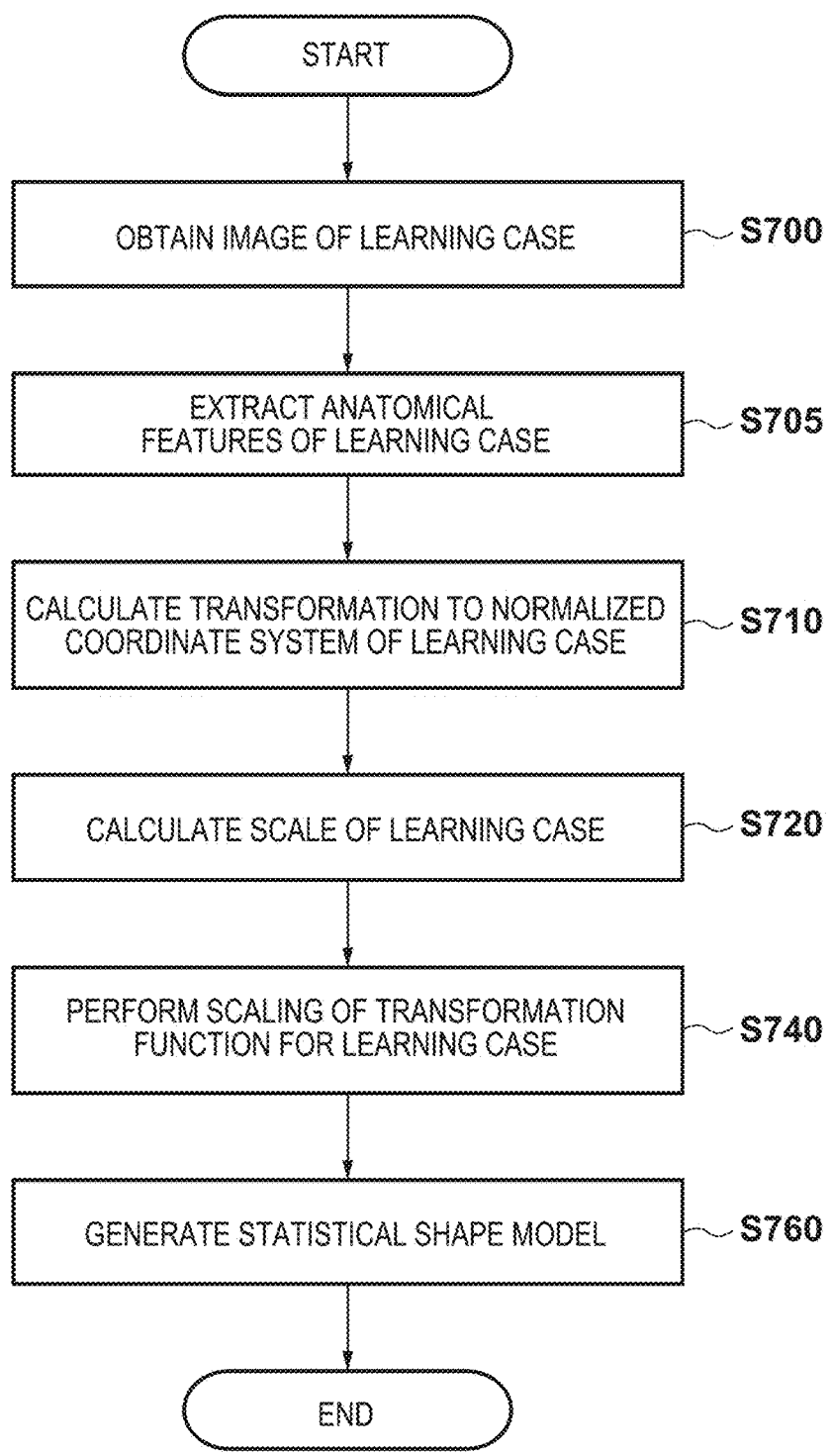
FIG. 13 is a flowchart showing a processing procedure performed by a processing apparatus according to the fourth embodiment.

The overall operation of the processing apparatus 800 will be described next. In this embodiment, a CPU 211 executes programs stored in a main memory 212 to implement the functions of the respective units. In addition, the result of each process performed by the processing apparatus 200 to be described below is recorded by being stored in the main memory 212. FIG. 13 is a flowchart for explaining a processing procedure performed by the processing apparatus 800 according to this embodiment. This procedure will be described with reference to FIG. 13.

(Step S700) Obtaining of Image of Learning Case

In step S700, the image obtaining unit 1000 obtains prone position MRI images of learning cases. In this embodiment, the image obtaining unit 1000 obtains prone position MRI images of $N_{samples}$ learning cases. Processing similar to that in step S300 in the first embodiment is applied to each of the $N_{samples}$ learning cases. A detailed description of this processing will be omitted.

(Step S705) Extraction of Anatomical Features of Learning Cases

In step S705, the anatomical feature extraction unit 1020 extracts anatomical features of each learning case by processing each of the prone position MRI images of the learning cases obtained in step S700. The anatomical feature extraction unit 1020 applies processing similar to that in step S310 in the first embodiment to each of the $N_{samples}$ learning cases. A detailed description of the processing will be omitted.

(Step S710) Calculation of Transformation to Normalized Coordinate System of Learning Case In step S710, the normalization unit 1040 derives a normalization transformation for transforming the shape of the object in each of a plurality of learning cases to a reference shape. More specifically, the normalization unit 1040 calculates a coordinate transformation function from the MRI image coordinate system to the normalized coordinate system. The normalization unit 1040 applies processing similar to that in step S320 in the first embodiment to each of the $N_{samples}$ learning cases. A detailed description of the processing will be omitted.

In this embodiment, a calculated transformation to the normalized coordinate system is expressed as a function $\phi_{p,j}(x)$. In this case, the function $\phi_{p,j}(x)$ is calculated for each case, and is a transformation function from the prone position MRI image coordinate system to the prone position normalized coordinate system for each case. A transformation from the prone position normalized coordinate system to the prone position MRI image coordinate system is also calculated in the same manner as in the first embodiment. This transformation is expressed as $\phi^{-1}_{p,j}(x)$ where j is an index of the case number of a learning case, and $1 \leq j \leq N_{samples}$ in this embodiment. Note that in the embodiment, with regard to each learning case, a prone position MRI image or a prone position MRI image coordinate system has been translated in advance to match the nipple position in the image with the origin of the coordinate system.

(Step S720) Calculation of Scale of Each Learning Case

In step S720, the scale calculation unit 1620 calculates a scale of each learning case. The scale calculation unit 1620 executes this processing in the same manner as in step S550 in the third embodiment. A detailed description of the processing will be omitted. Each calculated scale is expressed as $v_j$ ($1 \leq j \leq N_{samples}$).

(Step S740) Scaling of Transformation Function

In step S740, the statistical shape model generation unit 1640 calculates a transformation function $\phi'^{-1}_{p,j}(x)$ by scaling the transformation function $\phi^{-1}_{p,j}(x)$ based on the transformation function $\phi^{-1}_{p,j}(x)$ concerning $N_{samples}$ cases and the scale $v_j$. More specifically, the statistical shape model generation unit 1640 calculates the transformation function $\phi'^{-1}_{p,j}(x)$ according to equation (26).

$$\phi'^{-1}_{p,j}(x') = \phi^{-1}_{p,j}(x)/v_j \quad (26)$$

In this case, if $x=(x, y, z)^T$, $x'=(xXv_j, y, zXv_j)^T$. That is, $\phi'^{-1}_{p,j}(x)$ is a function obtained by scaling $\phi^{-1}_{p,j}(x)$ with the scale value $v_j$ of each learning case in the directions of x-coordinates and z-coordinates in the domain and further scaling the value of the function with the scale value $v_j$. The statistical shape model generation unit 1640 calculates the transformation function $\phi'_{p,j}(x)$ ($1 \leq j \leq N_{samples}$) by executing the above processing for the transformation functions $\phi^{-1}_{p,j}(x)$ ($1 \leq j \leq N_{samples}$) Of all the $N_{samples}$ cases and scaling each case.

(Step S760) Generation of Statistical Shape Model

In step S760, the statistical shape model generation unit 1640 generates a statistical shape model by statistically processing the transformation function $\phi'^{-1}_{p,j}(x)$ ($1 \leq j \leq N_{samples}$) calculated in step S740. A detailed description of this processing will be omitted.

First of all, the statistical shape model generation unit 1640 discretizes the transformation function $\phi'^{-1}_{p,j}(x)$. The statistical shape model generation unit 1640 executes processing similar to that in step S5820 in the third embodiment, targeted to $\phi'_{ps,j}(x)$, with respect to the transformation function $\phi'^{-1}_{p,j}(x)$ in this embodiment. A detailed description of this processing will be omitted. The discretized vectors obtained by the processing are respectively represented by $q_{x,j}$, $q_{y,j}$, and $q_{z,j}$. The statistical shape model generation unit 1640 applies this processing to all the $N_{samples}$ transformation functions $\phi'^{-1}_{p,j}(x)$. In this case, the calculated discretized vectors $q_{x,j}$, $q_{y,j}$, and $q_{z,j}$ are vectors obtained by sampling transformation functions in the normalized coordinate system. In the normalized coordinate system, each learning case has an anatomically almost matching positional relationship. For this reason, the values of these discretized vectors in the same dimension have the values of the transformation functions at anatomically almost the same positions in the respective learning cases.

The statistical shape model generation unit 1640 then generates a statistical shape model by statistically processing the calculated discretized vectors $q_{x,j}$, $q_{y,j}$, and $q_{z,j}$ ($1 \leq j \leq N_{samples}$) by principal component analysis. The statistical shape model generation unit 1640 performs this processing in the same manner as in step S5840 in the third embodiment. A detailed description of the processing will be omitted. The average vectors obtained by the above processing are respectively expressed as $e'_{ave,x}$, $e'_{ave,y}$, and $e'_{ave,z}$. In addition, the obtained eigenvectors are respectively expressed as $e'_{x,k}$, $e'_{y,k}$, and $e'_{z,k}$, where k is the index of an eigenvector obtained by principal component analysis. When obtaining $N'_{mode}$ eigenvectors, $1 \leq k \leq N_{mode}$.

With the processing in steps S700 to S760 described above, the processing apparatus 800 according to this embodiment generates a statistical shape model based on learning cases. This statistical shape model is a model for efficiently approximating the transformation function $\phi'^{-1}_{p,j}(x)$ of each learning case with a small number of bases, as indicated by equation (20) described concerning step S5840 in the third embodiment. This model is generated in consideration of statistical characteristics common to the learning cases. Even if an unknown case which is not included in the learning cases is provided, the model can be expected to accurately approximate a transformation function for the case. In this case, the transformation function is a function having a normalized coordinate system as a domain. Since the positions of the body surface and pectoralis major muscle surface in the normalized coordinate system are known, the statistical shape model can be used in the following manner.

That is, it is possible to obtain a factor vector of a statistical shape model such that the shapes of the body surface and pectoralis major muscle surface which are extracted from a prone position MRI image of an unknown case almost match the shapes of the body surface and pectoralis major muscle surface represented by the statistical shape model. In this case, the shapes of the body surface and pectoralis major muscle surface which are extracted from the prone position MRI image of the unknown case may partially include an information loss or noise. That is, a factor vector can be obtained from limited observation information concerning the shapes of the body surface and pectoralis major muscle surface from the prone position MRI image of the unknown case. Calculating a factor vector makes it possible to estimate a transformation function for the unknown case and hence to generate information compensating for the limited observation information. That is, the statistical shape model can be used for segmentation of the breast region.

[Fifth Embodiment]

This embodiment will exemplify a processing apparatus 900 which constructs both a statistical deformation model described in the third embodiment and a statistical shape model described in the fourth embodiment, and simply and robustly executes normalization processing for a target case by using these models.

(Functional Arrangement)

Figure 14:
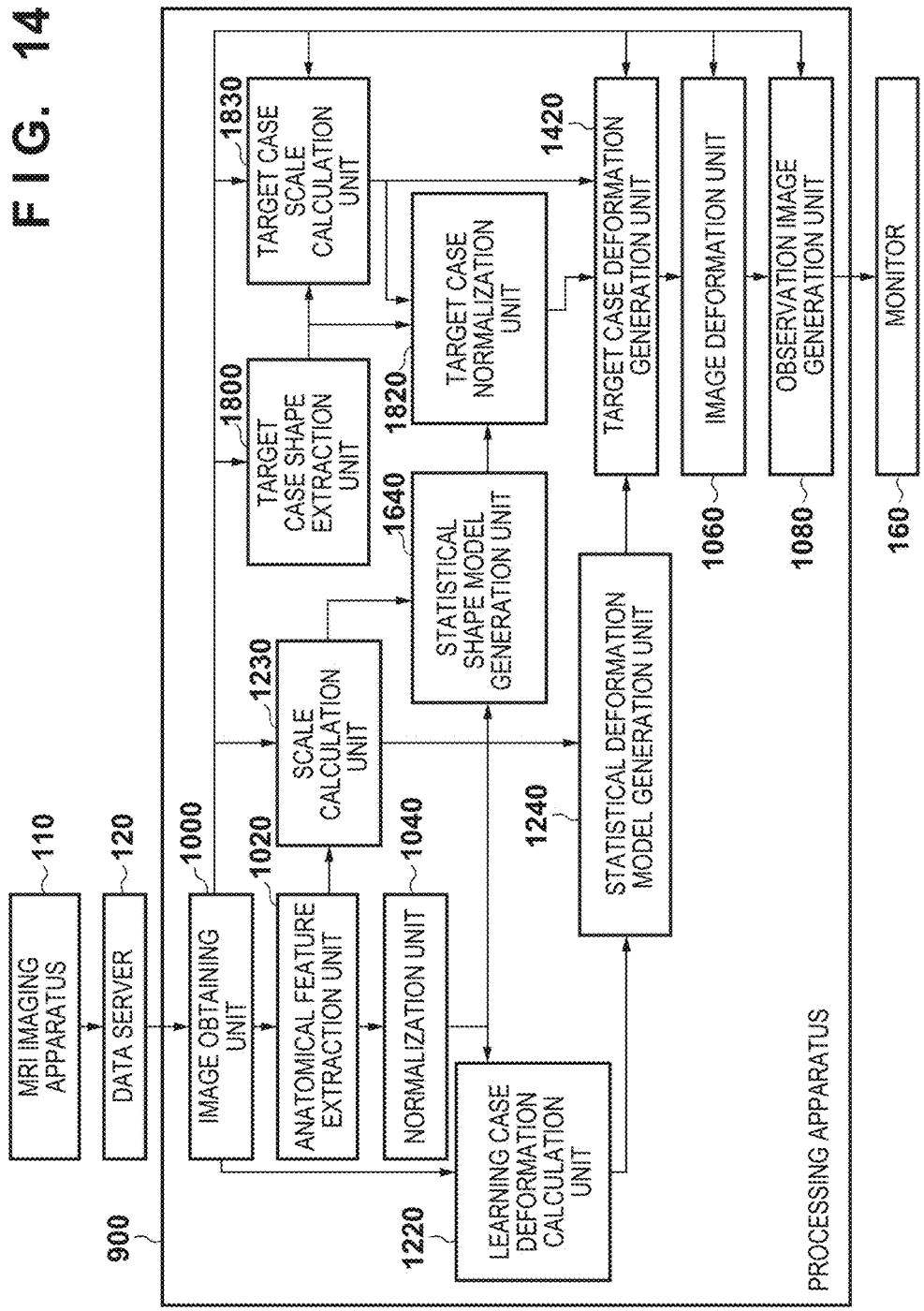
FIG. 14 is a block diagram showing the functional arrangement of a processing system according to the fifth embodiment.

FIG. 14 is a block diagram showing the arrangement of a processing system according to this embodiment. In the embodiment, the same reference numerals denote constituent elements having the same functions as in the first to fourth embodiments, and a description of them will be omitted. As shown in FIG. 14, the processing apparatus 900 according to the embodiment includes an image obtaining unit 1000, an anatomical feature extraction unit 1020, a normalization unit 1040, a scale calculation unit 1230, a statistical shape model generation unit 1640, and a statistical deformation model generation unit 1240. The processing apparatus 900 further includes a target case shape extraction unit 1800, a target case normalization unit 1820, a target case scale calculation unit 1830, a target case deformation generation unit 1420, an image deformation unit 1060, and an observation image generation unit 1080.

The target case shape extraction unit 1800 extracts the body surface and pectoralis major muscle surface shapes of a target case from an MRI image of the target case obtained by the image obtaining unit 1000. The target case scale calculation unit 1830 calculates a scale of the target case based on the MRI image of the target case obtained by the image obtaining unit and the body surface and pectoralis major muscle surface shapes of the target case extracted by the target case shape extraction unit 1800. The target case normalization unit 1820 calculates a transformation to the normalized coordinate system of the target case based on a statistical shape model generated by the statistical shape model generation unit 1640, the shapes of the body surface and pectoralis major muscle surface of the target case extracted by the target case shape extraction unit 1800, and the scale of the target case calculated by the target case scale calculation unit 1830.

(Processing Procedure)

The overall operation performed by the processing apparatus 900 will be described next. In this embodiment, a CPU 211 executes programs stored in a main memory 212 to implement the functions of the respective units. In addition, the result of each process performed by the processing apparatus 900 to be described below is recorded by being stored in the main memory 212. Processing performed by the processing apparatus 900 in the embodiment includes processing in the learning phase and processing in deformation estimation phase. The processing apparatus 900 executes processing in the learning phase first, and then execute processing in the deformation estimation phase. In the processing in the learning phase, the processing apparatus 900 learns deformations between MRI images of many cases in the prone position and the supine position, and generates a statistical deformation model. In addition, in the processing in the learning phase, the processing apparatus 900 learns the shapes of the prone position and supine position shapes of many cases and generates a statistical shape model. In the processing in the deformation estimation phase, the processing apparatus 900 executes deformation alignment between the prone position and the supine position of the target case by using the statistical deformation model and the statistical shape model generated in the learning phase.

The following description of this embodiment will exemplify a case in which the processing apparatus 900 executes both processing in the learning phase and processing in the deformation estimation phase. However, different processing apparatuses may execute processing in the learning phase and processing in the deformation estimation phase. In addition, the processing apparatus 900 according to the embodiment may execute, for example, only the processing in the learning phase instead of executing both the processing in the learning phase and the processing in the deformation estimation phase. In addition, the provision of a statistical deformation model and a statistical shape model obtained as a result of the processing in the learning phase itself is incorporated in the embodiment.

(Processing in Learning Phase)

Figure 15:
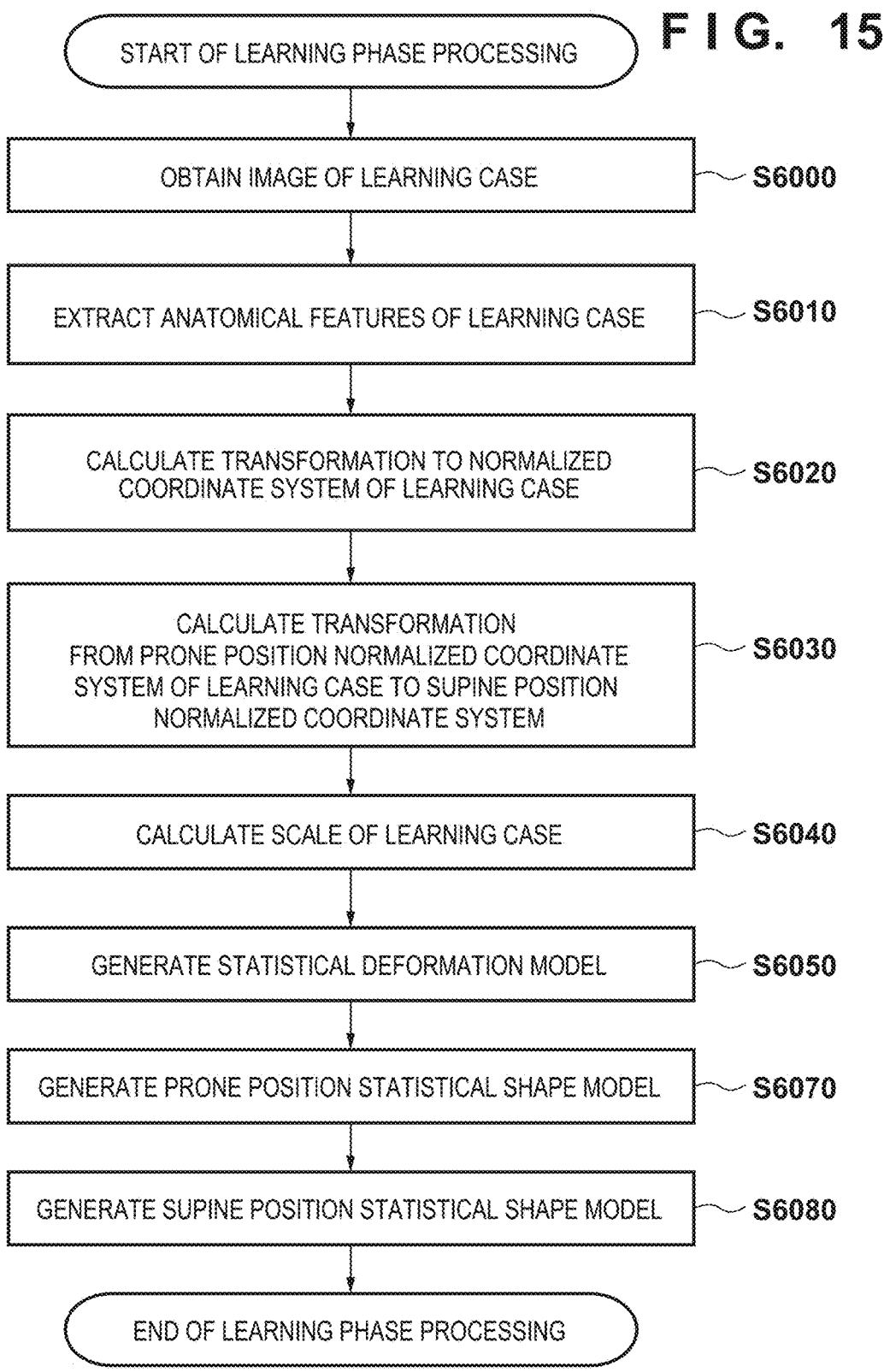
FIG. 15 is a flowchart showing a processing procedure in a learning phase in a processing apparatus according to the fifth embodiment.

FIG. 15 is a flowchart for explaining a processing procedure in the learning phase which is performed by the processing apparatus 900 according to this embodiment. The processing will be described along FIG. 15.

(S6000) to (S6050)

In steps S6000 to S6050, the processing apparatus 900 executes the same processing as that in steps S500 to S580 executed by the processing apparatus 200 in the third embodiment. A scale value of a learning case calculated in step S6040 is expressed as $v_j$, where j is an index of the case number of a learning case, and $1 \leq j \leq N_{samples}$ in this embodiment. In addition, average vectors of a statistical deformation model generated in step S6050 are respectively expressed as $e_{deform\ ave,x}$, $e_{deform\ ave,y}$, and $e_{deform\ ave,z}$, and eigenvectors are respectively expressed as $e_{deform,x,k}$, $e_{deform\ y,k}$ and $e_{deform\ z,k}$, where k is an index of a plurality of eigenvectors obtained by principal component analysis. Assume that in this embodiment, $N_{deform\ mode}$ eigenvectors are obtained. That is, $1 \leq k \leq N_{deform\ mode}$. A detailed description of this processing will be omitted.

(S6070) Generation of Prone Position Statistical Shape Model

In step S6070, the statistical shape model generation unit 1640 generates a statistical shape model concerning the shapes of learning cases in the prone position by executing the same processing as that in steps S740 and S760 in the fourth embodiment with respect to the shapes of the learning cases in the prone position. In this processing, a scale value used for the scaling of each learning case is the scale value $v_j$ calculated in step S6040. With the above processing, a prone position statistical shape model is generated. Average vectors of the prone position statistical shape model generated in this case are respectively expressed as $e_{p\ shape,ave,x}$, $e_{p\ shape,ave,y}$, and $e_{p\ shape,ave,z}$, and eigenvectors are respectively expressed as $e_{p\ shape,x,k}$, $e_{p\ shape,y,k}$, and $e_{p\ shape,z,k}$, where k is an index of a plurality of eigenvectors obtained by principal component analysis. Assume that in this embodiment, $N_{p\ shape\ mode}$ eigenvectors are obtained. That is, $1 \leq k \leq N_{p\ shape\ mode}$. A detailed description of this processing will be omitted to void the repeated description of the processing in steps S740 and S760 in the fourth embodiment.

(S6080) Generation of Supine Position Statistical Shape Model

In step S6080, the statistical shape model generation unit 1640 generates a statistical shape model concerning the shapes of learning cases in the supine position by executing the same processing as that in steps S740 and S760 in the fourth embodiment with respect to the shapes of the learning cases in the supine position. In this processing, a scale value used for the scaling of each learning case is the scale value $v_j$ calculated in step S6040.

With the above processing, a supine position statistical shape model is generated. Average vectors of the supine position statistical shape model generated in this case are respectively expressed as $e_{s\ shape,ave,x}$, $e_{s\ shape,ave,y}$, and $e_{s\ shape,ave,z}$, and eigenvectors are respectively expressed as $e_{s\ shape,x,k}$, $e_{s\ shape,y,k}$, and $e_{s\ shape,z,k}$, where k is an index of eigenvectors obtained by principal component analysis. Assume that in this embodiment, $N_{s\ shape\ mode}$ eigenvectors are obtained. That is, $1 \leq k \leq N_{s\ shape\ mode}$. A detailed description of this processing will be omitted to void the repeated description of the processing in steps S740 and S760 in the fourth embodiment. With the above processing, the processing apparatus 900 generates the statistical deformation model and prone position and supine position statistical shape models concerning the learning cases.

(Processing in Deformation Estimation Phase)

Figure 16:
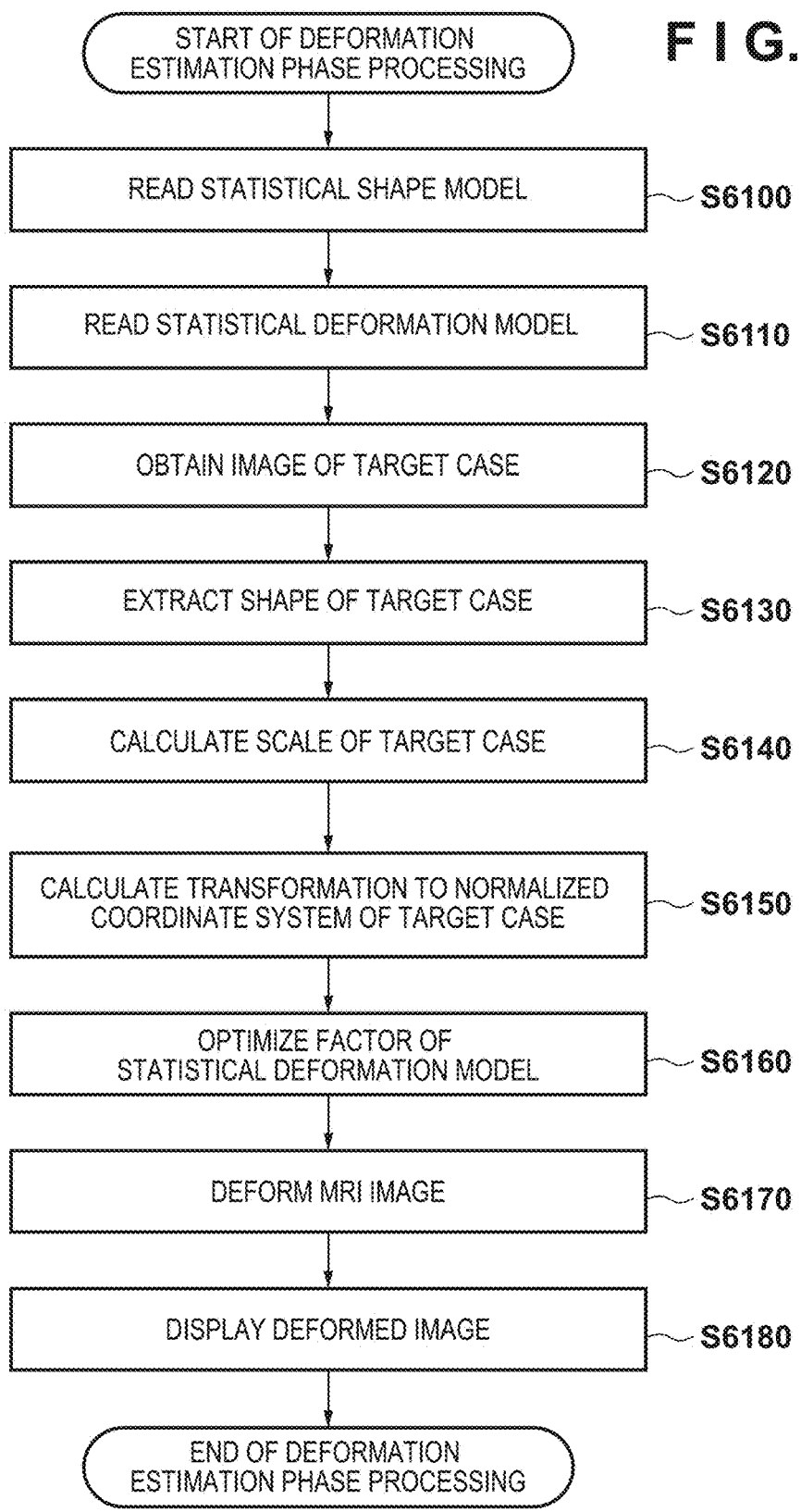
FIG. 16 is a flowchart showing a processing procedure in a deformation estimation phase in the processing apparatus according to the fifth embodiment.

A processing procedure in the deformation estimation phase executed by the processing apparatus 900 will be described next with reference to the flowchart of FIG. 16.

(S6100)

In step S6100, the processing apparatus 900 reads out the prone position and supine position statistical shape models generated by the processing in the learning phase from the main memory 212 of the processing apparatus 900.

From (S6110) to (S6120): Reading of Statistical Deformation Model/Obtaining of Image of Target Case In steps S6110 to S6120, the processing apparatus 900 executes the same processing as that in steps S600 to S602 which is executed as processing in the deformation estimation phase by the processing apparatus 200 according to the third embodiment. A description of this processing will be omitted.

(S6130) Extraction of Shape of Target Case

In step S6130, the target case shape extraction unit 1800 extracts the shapes of the body surface and pectoralis major muscle surface of the target case in the prone position and the supine position by processing the prone position MRI image and the supine position MRI image of the target case which are obtained in step S6120. More specifically, the target case shape extraction unit 1800 extracts a plurality of point groups representing the positions of the body surface and pectoralis major muscle surface from each MRI image. This processing is partly the same as that in step S604 executed by the processing apparatus 200 according to the third embodiment. Note however that the above shape extraction processing need not be targeted to the entire breast region of the object depicted in each MRI image, and it is only required to detect the shape of part of the breast region or its peripheral region. In addition, a shape to be extracted need not be a dense point group like the extraction result of anatomical features described as the processing in step S604 in the third embodiment, and may be a relatively sparse point group. In this embodiment, the extracted prone position shape is expressed as $s_{p,surface,i}$ ($1 \leq i \leq N_{p,surface}$), and the extracted supine position shape is expressed as $s_{s,surface,i}$ ($1 \leq i \leq N_{s,surface}$). In this case, $N_{p,surface}$ represents the number of points representing the prone position shape. Likewise, $N_{s,surface}$ represents the number of points representing the supine position shape.

In addition, in step S6130, while executing the above processing, the target case shape extraction unit 1800 obtains nipple positions and reference positions on the pectoralis major muscle surface of the target case in the prone position and the supine position. This processing is executed, for example, in the following manner. The processing apparatus 900 displays a prone position MRI image and a supine position MRI image on a monitor 160. The user designates positions on the displayed screen with a mouse 170 and a keyboard 180. The target case shape extraction unit 1800 then obtains the designation results.

(S6140) Calculation of Scale of Target Case

In step S6140, the target case scale calculation unit 1830 executes the same processing as that executed for a learning case in step S6040 in the learning phase in this embodiment with respect to the target case. With this processing, the target case scale calculation unit 1830 calculates a scale $v_{target}$ of the target scale.

(S6150) Normalization Using Statistical Shape Model

In step S6150, the target case normalization unit 1820 optimizes parameters of the statistical shape model for the target case based on the prone position shape $s_{p,surface,i}$, the supine position shape $s_{s,surface,i}$, and the scale $v_{target}$ of the target case, and calculates a transformation to the normalizing coordinate system.

More specifically, the target case normalization unit 1820 executes the following processing. First of all, the target case normalization unit 1820 optimizes a parameter concerning the prone position statistical shape model obtained in step S6070. In this case, the parameter is a weighting factor for a plurality of eigenvectors of the statistical shape model, and a vector having a dimension equal in number to the number of eigenvectors. The value of this vector is optimized based on the following criterion. This is the criterion that minimizes the difference between a position indicated by a prone position shape $s_{p,surface,i}'$ in the normalized coordinate system and a reference shape in the normalized coordinate system when the prone position shape $s_{p,surface,i}$ in the prone position MRI image is transformed to the prone position shape $s_{p,surface,i}'$. That is, the target case normalization unit 1820 optimizes the parameter of the statistical shape model so as to properly map the prone position shape $s_{p,surface,i}$ to the reference shape.

A prone position statistical shape model in this embodiment is a model expressing a transformation from the prone position normalized coordinate system to the prone position MRI image coordinate system. For this reason, specifically, the above optimization processing is executed in the following procedure. First of all, the target case normalization unit 1820 expresses the shapes of the body surface and pectoralis major muscle surface in the prone position normalized coordinate system by an arbitrary shape expression using point groups or polygons. Note that in this embodiment, both the shapes of the body surface and pectoralis major muscle surface in the prone position normalized coordinate system are planes. The target case normalization unit 1820 then sets an arbitrary initial value to the parameter of the prone position statistical shape model and transforms the shapes of the body surface and pectoralis major muscle surface to those in the prone position MRI image coordinate system by using the prone position statistical shape model expressed by the parameter. The target case normalization unit 1820 evaluates the differences between the shapes of the transformed body surface and pectoralis major muscle surface and the shape $s_{p,surface,i}$ in the prone position MRI image coordinate system. The target case normalization unit 1820 variously changes the parameter of the prone position statistical shape model to search for a parameter that minimizes the above difference evaluation. That is, the target case normalization unit 1820 optimizes the parameter of the prone position statistical shape model by repeated processing based on the above difference evaluation.

Note that in the above processing, scaling is performed between the coordinate values of the shape $s_{p,surface,i}$ in the prone position MRI image coordinate system of the target case and the statistical shape model in consideration of the scale $v_{target}$ calculated in step S6140. Likewise, when processing a supine position statistical shape model, the target case normalization unit 1820 optimizes the parameter of the supine position statistical shape model obtained in step S6080 based on the supine position shape $s_{s,surface,i}$.

With the above processing, the parameters of the statistical shape models concerning the prone position and the supine position are optimized with respect to the shape of the target case. This will calculate a transformation $\phi_{p,target}(x)$ to the normalized coordinate system concerning the prone position of the target case and a transformation $\phi_{s,target}(x)$ to the normalized coordinate system concerning the supine position.

From (S6160) to (S6180) Optimization of Statistical Deformation Model/MRI Image Deformation/Display In steps S6160 to S6180, the processing apparatus 900 executes the same processing as that in steps S640 to S660 executed by the processing apparatus 200 according to the third embodiment. A detailed description of this processing will be omitted.

With the processing in steps S6100 to S6180 described above, the processing in the deformation estimation phase in this embodiment is executed. As a result of this processing, deformation estimation processing is executed between the prone position MRI image and the supine position MRI image of the target case. A deformed MRI image is generated by deforming the prone position MRI image so as to correspond to the supine position MRI image and is displayed together with the supine position MRI image, thereby presenting an input image in a form that allows easy comparison.

As compared with the processing apparatus according to the third embodiment, the processing apparatus according to the fifth embodiment obviates the necessity to extract anatomical features including information concerning dense point groups representing the body surface shape and pectoralis major muscle surface shape of the target case, and is only required to extract relatively sparse body surface shape and pectoralis major muscle surface shape. This is because, even if point groups representing the body surface shape and the pectoralis major muscle surface shape are spatially sparse, it is possible to estimate the parameter of the statistical shape model, and to calculate a transformation from the MRI image coordinate system to each normalized coordinate system based on the parameter. This makes it possible to execute deformation alignment between the two images even if it is difficult to extract dense point groups representing the body surface shape and the pectoralis major muscle surface shape because of the influences of the image quality and the like of each MRI image of the target case.

(First Modification of Fifth Embodiment) Switching Between Use and Nonuse of Statistical Shape Model This embodiment has exemplified the case in which both a prone position statistical shape model and a supine position statistical shape model are used in the deformation estimation phase. However, one of the models may be used. For example, the same processing as that in step S604 in the third embodiment may be executed as processing concerning one of the prone position and the supine position in the processing of step S6130. In this case, when performing the processing in step S6150 as subsequent processing, the processing of calculating a transformation to the normalized coordinate system concerning one of the above prone position and the supine position may be performed as the same processing as that in step S610 in the third embodiment. This makes it possible to more accurately calculate a transformation from the MRI image coordinate system to the normalized coordinate system when a dense body surface shape and pectoralis major muscle surface shape of the target case in one of the prone position and the supine position can be obtained.

In addition, any of the methods in this embodiment and the above modification may be switched and executed based on an extraction result on the anatomical features of the target case. Assume that while the processing method described in the third embodiment is executed as standard processing, it is difficult or expected to be difficult to extract a dense body surface shape and pectoralis major muscle surface shape from an MRI image of a target case. In this case, the processing in this embodiment and the processing in the above modification may be selectively executed. This makes it possible to selectively use a proper processing method in consideration of the image quality and the like of the MRI image of the target case. It is therefore possible to more robustly perform deformation alignment of the target case.

In addition, this embodiment is not limited to the case in which MRI images of the target case in both the prone position and the supine position are obtained. For example, the embodiment can be applied to a case in which no MRI image of the target case in one of the prone position and the supine position can be obtained, and only a relatively sparse body surface shape can be obtained. Assume that no MRI image of a target case in the supine position is obtained, and the body surface of the target case in the supine position is measured by using a stylus or the like capable of position measurement. In this case, an MRI image concerning the prone position of the target case is obtained in step S6120 in the processing in the deformation estimation phase, and the same processing as that in step S604 in the third embodiment associated with the supine position is executed in the processing of step S6130, and a sparse body surface shape measured by using the stylus or the like is obtained concerning the supine position. In step S6150, the processing of calculating a transformation to the normalized coordinate system concerning the prone position is executed in the same manner as in step S610 in the third embodiment. With regard to the supine position, the processing in step S6150 in this embodiment is executed based on the sparse body surface shape. The processing in and after step S6160 is executed in the same manner as described in the embodiment.

The above method can deform and display a prone position MRI image of the target case so as to match the body surface shape of the target case in the supine position and the shape of the pectoralis major muscle surface in the supine position estimated based on a statistical shape model. According to the above method, for example, it is possible to effectively support a surgical operation on the target case. More specifically, it is possible to deform and display an MRI image of the target case in the prone position which is imaged before the surgical operation based on the body surface shape measured at the time of the surgical operation executed in the supine position. This makes it possible to present the user with the specific position of a region of interest or the like on a prone position MRI image at the time of a surgical operation in the supine position.

(Second Modification of Fifth Embodiment) Prone Position/Supine Position Integrated Model This embodiment has exemplified the case in which the statistical shape model generation unit 1640 separately constructs statistical shape models concerning the prone position and the supine position. However, this is no exhaustive. For example, the statistical shape model generation unit 1640 may construct an integrated shape model by integrating information concerning a prone position shape and information concerning a supine position shape. More specifically, as processing in the learning phase, the following processing is executed in place of the processing in steps S6070 and S6080. That is, the statistical shape model generation unit 1640 executes calculation processing for discretized vectors $q_{x,j}$, $q_{y,j}$, and $q_{z,j}$, which is executed by the processing apparatus 800 described in the fourth embodiment in step S760, with respect to each of the prone position and supine position of a learning case. In this case, discretized vectors calculated concerning the prone position are respectively expressed as $q_{px,j}$, $q_{py,j}$, and $q_{pz,j}$, and discretized vectors calculated concerning the supine position are respectively expressed as $q_{sx,j}$, $q_{sy,j}$, and $q_{sz,j}$.

The statistical shape model generation unit 1640 then calculates a vector by combining these six vectors for each learning case, and then calculates average vectors and eigenvectors by executing principal component analysis of the vector group. These pieces of information will be referred to as a prone position/supine position integrated shape model in this embodiment. The prone position/supine position integrated shape model is a model representing both a transformation from the prone position MRI image coordinate system concerning a learning case to the prone position normalized coordinate system and a transformation from a supine position MRI image coordinate system to a supine position normalized coordinate system. This model is also a model describing statistical characteristics between two transformations. In the deformation estimation phase, the following processing is executed in place of the processing in step S6150. That is, the target case normalization unit 1820 calculates transformations from the prone position and supine position MRI image coordinate systems to the respective normalized coordinate systems by optimization processing for the parameters of the above model. This makes it possible to calculate transformations from the prone position and supine position of the target case to the respective normalized coordinate systems in consideration of statistical characteristics between the transformations, thereby executing transformations to the normalized coordinate systems more accurately.

In addition, a transformation from one of the prone position and supine position of a target case to one of the normalized coordinate systems can be calculated separately (by, for example, the method described in the fourth embodiment), the other transformation can be estimated by using the above prone position/supine position integrated shape model. For example, even if one of the shapes of a target case in the prone position and the supine position cannot be extracted, using the above integrated shape model can estimate a transformation to the other normalized coordinate system. This makes it possible to execute processing in and after step S6160 in the processing in the deformation estimation phase. According to this method, even if an MRI image of a target case in one of the prone position and the supine position cannot be obtained, it is possible to implement statistically likelihood deformation of an MRI image of the target case in a posture allowing the obtaining of an MRI image to an MRI image in the other posture.

[Sixth Embodiment]

The fifth embodiment has exemplified the case in which a statistical deformation model and statistical shape models concerning the prone position and the supine position are generated, and a deformation between the prone position MRI image and supine position MRI image of a target case is estimated by using each model. The sixth embodiment will exemplify a method of generating a model by integrating transformations from prone position and supine position MRI image coordinate systems to the respective normalized coordinate systems and a deformation between the respective normalized coordinate systems and estimating a deformation between the prone position MRI image and the supine position MRI image of the target case by using the generated model. In this embodiment, a generated model will be referred to as a statistical model.

(Functional Arrangement)

Figure 17:
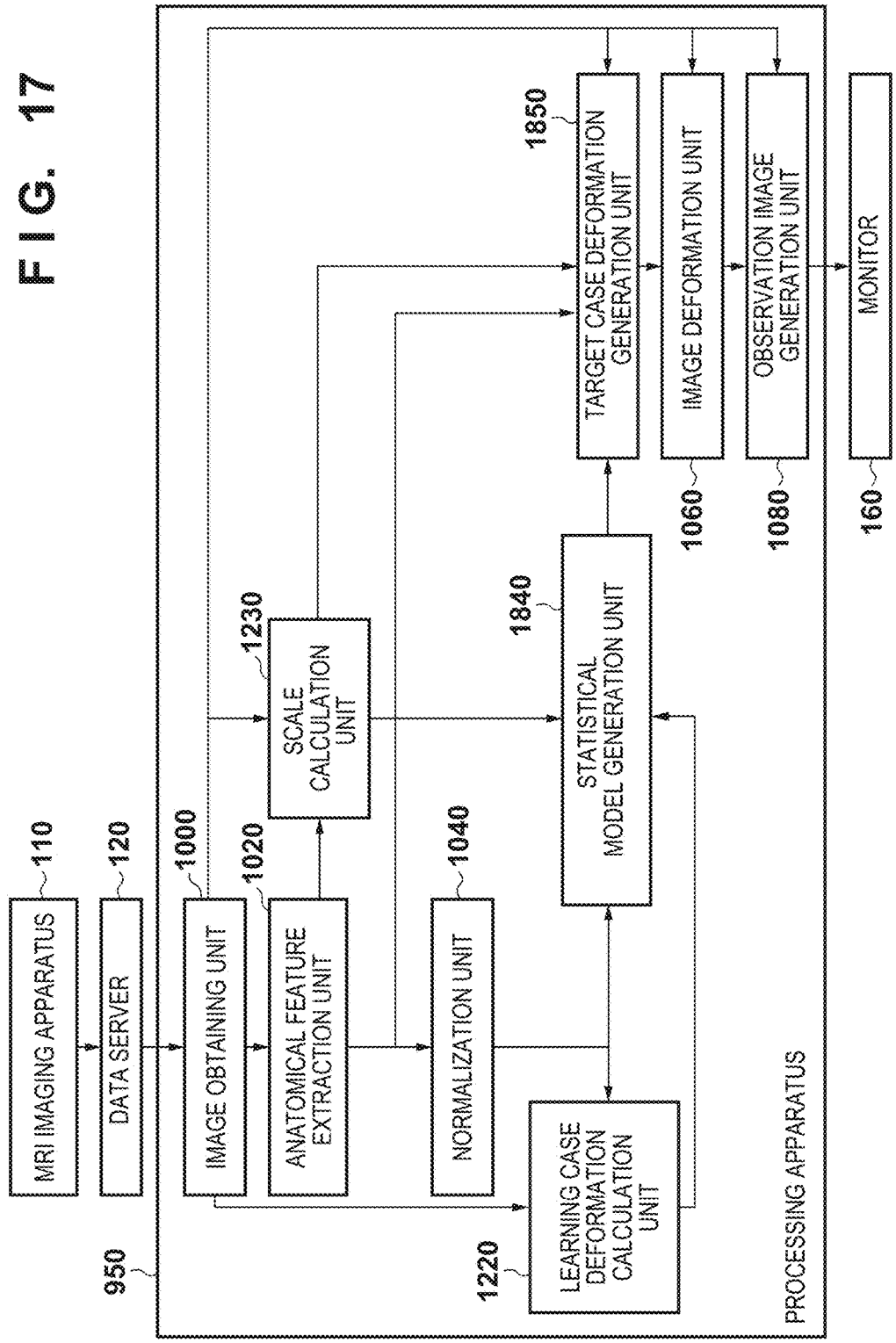
FIG. 17 is a block diagram showing the functional arrangement of a processing system according to the sixth embodiment.

FIG. 17 is a block diagram showing the functional arrangement of a processing apparatus 950 according to this embodiment. Referring to FIG. 17, the same reference numerals as those in the first to fifth embodiments denote constituent elements having the same functions as in the respective embodiments, and a description of them will be omitted. A statistical model generation unit 1840 generates a statistical model of learning cases based on the results of processing executed by a normalization unit 1040, a learning case deformation generation unit 1220, and a scale calculation unit 1230. A target case deformation generation unit 1850 generates a deformation of a target case based on the statistical model generated by the statistical model generation unit 1840, the anatomical features of the target case extracted by an anatomical feature extraction unit 1020, and the scale calculated by the scale calculation unit 1230.

(Processing Procedure)

The overall operation performed by the processing apparatus 950 will be described next. In this embodiment, a CPU 211 executes programs stored in a main memory 212 to implement the functions of the respective units. In addition, the result of each process performed by the processing apparatus 200 to be described below is recorded by being stored in the main memory 212. Processing performed by the processing apparatus 950 according to this embodiment includes processing in a learning phase and processing in a deformation estimation phase as in the fifth embodiment. The processing apparatus 950 executes the processing in the learning phase first, and then executes the processing in the deformation estimation phase as in the fifth embodiment. In the processing in the learning phase, the processing apparatus 950 learns deformations between prone position and supine position MRI images of many cases and generates a statistical model. In the processing in the deformation estimation phase, the processing apparatus 950 executes deformation alignment between the prone position and the supine position of the target case by using the statistical model generated in the learning phase.

(Processing in Learning Phase)

Figure 18:
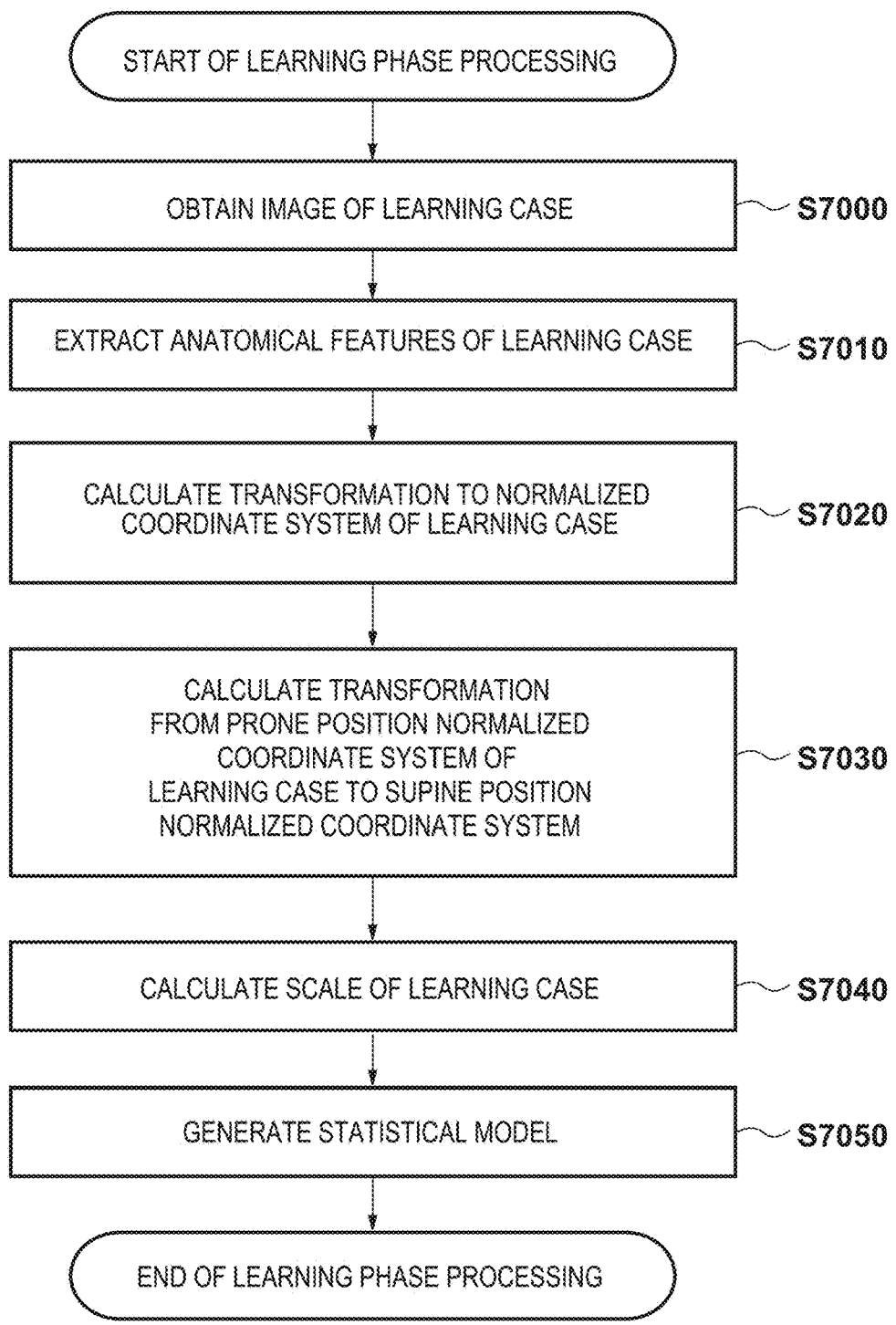
FIG. 18 is a flowchart showing a processing procedure in a learning phase in a processing apparatus according to the sixth embodiment.

FIG. 18 is a flowchart for explaining a processing procedure in the learning phase performed by the processing apparatus 950 according to this embodiment. Processing in the learning phase according to the embodiment will be described in detail below in accordance with the processing procedure shown in this flowchart.

From (S7000) to (S7040)

The processing apparatus 950 executes processing in steps S7000 to S7040 in the same manner as in steps S6000 to S6040 executed by the processing apparatus 900 according to the fifth embodiment. A detailed description of this processing will be omitted.

(S7050)

In step S7050, the statistical model generation unit 1840 generates a statistical model. This processing will be described in detail. First of all, the statistical model generation unit 1840 executes processing similar to part of the processing in steps S740 and S760 in the fourth embodiment with respect to each of the prone position and supine position of each learning case, and calculates discretized vectors concerning a transformation from the MRI image coordinate system to the normalized coordinate system. In this embodiment, discretized vectors concerning a transformation from the prone position MRI image coordinate system to the prone position normalized coordinate system are respectively expressed as $q_{p\_x,j}$, $q_{p\_y,j}$, and $q_{p\_z,j}$. Likewise, discretized vectors concerning a transformation from the supine position MRI coordinate system to the supine position normalized coordinate system are respectively expressed as $q_{s\_x,j}$, $q_{s\_y,j}$, and $q_{s\_z,j}$.

The statistical model generation unit 1840 then calculates discretized vectors $p_{x,j}$, $p_{y,j}$, and $p_{z,j}$ concerning deformation between the prone position and supine position of each learning case and the respective normalized coordinate systems. The statistical model generation unit 1840 executes this processing in the same manner as in steps S5800 and S5820 in the third embodiment. A detailed description of this processing will be omitted.

The statistical model generation unit 1840 then generates a vector by combining the vectors calculated for each case by the above method. The statistical model generation unit 1840 calculates an average vector and a plurality of eigenvectors by performing principal component analysis of the combined vector for each case. Thereafter, an average vector and a plurality of eigenvectors calculated by this processing will be referred to as a statistical model. This statistical model is used in the deformation estimation phase (to be described later). The weighted sum of the average vector and the plurality of eigenvectors of the statistical model describes statistical characteristics of a transformation from the MRI image coordinate system to the normalized coordinate system and a deformation between the respective normalized coordinate systems.

Processing in the learning phase in this embodiment is executed by the processing in steps S7000 to S7040 described above. As a result of this processing, a statistical model is generated.

(Processing in Deformation Estimation Phase)

Figure 19:
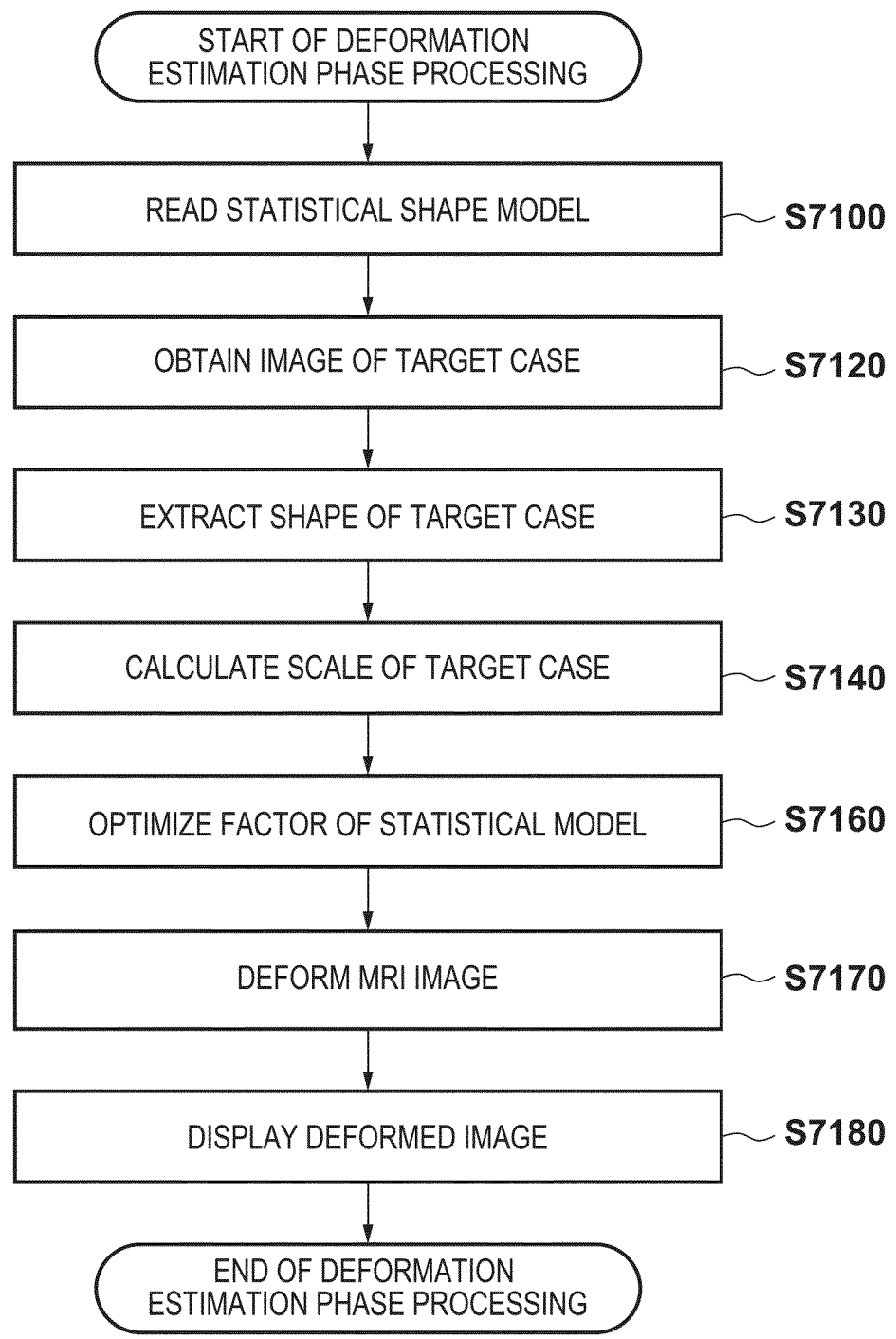
FIG. 19 is a flowchart showing a processing procedure in a deformation estimation phase in the processing apparatus according to the sixth embodiment.

FIG. 19 is a flowchart for explaining a processing procedure in the deformation estimation phase performed by the processing apparatus 950 according to this embodiment. The processing in the deformation estimation phase according to the embodiment will be described in detail in accordance with the processing procedure shown in this flowchart.

(S7100)

In step S6700, the processing apparatus 950 reads out the statistical model generated in the learning phase to the main memory 212.

From (S7120) to (S7140)

The processing apparatus 950 executes processing in steps S7120 to step S7140 in the same manner as in steps S6120 to S6140 executed by the processing apparatus 900 according to the fifth embodiment. A detailed description of this processing will be omitted.

(S7160)

In step S7160, the target case deformation generation unit 1850 generates a deformation of the target case based on the statistical model obtained in step S7100, the shapes of the body surface and pectoralis major muscle surface of the target case obtained in step S7130, and the scale calculated in step S7140. This processing will be described in detail below.

In this processing step, the target case deformation generation unit 1850 estimates a deformation by optimizing a parameter concerning the statistical model obtained in step S7100 with respect to the target case. The parameter in this case is a vector representing a weighting factor for the eigenvectors of the generated statistical model. The target case deformation generation unit 1850 computes the weighted linear sum of the average vector and eigenvectors of the statistical model based on the parameter to generate a transformation from the prone position and supine position MRI images to the normalized coordinate systems and a deformation between the respective normalized coordinate systems.

The parameter concerning the statistical model can be optimized based on an evaluation made by combining the following evaluation criteria. That is, parameter optimization can be performed by combining a criterion concerning the optimization of a statistical shape model (to be referred to as a criterion for normalization evaluation) described as the processing in step S6150 in the fifth embodiment and the evaluation function G (to be referred to as a criterion for deformation evaluation) described as the processing in step S640 in the third embodiment. More specifically, the target case deformation generation unit 1850 optimizes the parameter concerning the statistical model so as to minimize the evaluation value calculated based on both the criterion for normalization evaluation and the criterion for deformation evaluation or to maximize the evaluation value depending on the arrangement.

With the above processing, the parameter concerning the statistical model is optimized to estimate transformations from the prone position and supine position MRI image coordinate systems of the target case to the respective normalized coordinate systems and a deformation between the respective normalized coordinate systems.

From (S7170) to (S7180)

The processing apparatus 950 executes processing in steps S7170 to S7180 in the same manner as in steps S6170 to S6180 executed by the processing apparatus 900 according to the fifth embodiment. A detailed description of this processing will be omitted.

With the processing in steps S7100 to S7180 described above, the processing in the deformation estimation phase in this embodiment is executed. As a result of this processing, deformation estimation processing is executed between the prone position MRI image and the supine position MRI image of the target case. A deformed MRI image is generated by deforming the prone position MRI image so as to correspond to the supine position MRI image and is displayed together with the supine position MRI image, thereby presenting an input image in a form that allows easy comparison.

The processing apparatus according to this embodiment generates, in the learning phase, a statistical model having statistical characteristics of both transformations from the prone position and supine position MRI image coordinate systems concerning each learning case to the normalized coordinate systems and a deformation between the respective normalized coordinate systems. In this case, transformations from the MRI image coordinate systems to the normalized coordinate systems are mainly performed to absorb the differences in shape between the respective cases, and include by themselves information concerning the shape of each case. The embodiment is configured to generate a statistical model by performing principal component analysis of learning data as a pair of information concerning transformations from the MRI image coordinate systems to the normalized coordinate systems and a deformation between the respective normalized coordinate systems. This generates a model reflecting statistical characteristics between the shapes of the respective cases and deformation. It is therefore possible to estimate statistically likelihood deformation by deformation estimation using the statistical model generated in the deformation estimation phase in consideration of both the shape of the target case and deformation. This produces the effect of being able to perform deformation estimation with higher accuracy than the processing apparatus according to the fifth embodiment.

(First Modification of Sixth Embodiment) Formation of Hierarchal Model

This embodiment has exemplified the case in which in the processing in step S7050, the statistical model generation unit 1840 calculates discretized vectors concerning transformations from the MRI image coordinate systems concerning each learning case to the respective normalized coordinate systems and a deformation between the respective normalized coordinate systems, and generates a statistical model based on the vector obtained by combining the calculated discretized vectors. As a modification, however, like the processing apparatus 900 described in the fifth embodiment, the statistical model generation unit 1840 may calculate a statistical shape model and a statistical deformation model, and may additionally construct an upper model of the two models.

More specifically, first of all, as in the fifth embodiment, the statistical model generation unit 1840 generates a statistical shape model and a statistical deformation model. The statistical model generation unit 1840 then calculates, for each learning case, parameters when expressing transformations from the prone position and supine position MRI image coordinate systems to the respective normalized coordinate systems by using the statistical shape model. The calculated parameters are formed into vectors $b_{shape,j}$ ($1 \leq j \leq N_{samples}$). In addition, the statistical model generation unit 1840 generates, for each learning case, parameters when expressing deformations between the prone position and supine position normalized coordinate systems by using the statistical deformation model. The calculated parameters are formed into vectors $b_{deform,j}$ ($1 \leq j \leq N_{samples}$). The statistical model generation unit 1840 then generates vectors by combining the vectors $b_{shape,j}$ and $b_{deform,j}$ for each learning case, and performs principal component analysis with respect to the combined vectors. This can generate an upper model using the calculated average vector and a plurality of eigenvectors. In this case, in the deformation estimation phase, it is possible to estimate a deformation of a target case by estimating parameters concerning the upper model.

The above method allows the use of different numbers of eigenvectors between the statistical shape model and the statistical deformation model. This produces the effect of being able to more flexibly generate statistical models in addition to the effect of the processing apparatus 950 described in the sixth embodiment.

[Seventh Embodiment]

The first to sixth embodiments each have exemplified the case in which the human breast is a processing target. However, a processing target is not limited to the human breast. For example, a processing target may be the breast of an animal other than the human. Alternatively, a processing target may be another organ. When, for example, the heart is a target, the above embodiments can be applied by setting the region surrounded by the external wall and internal wall of the heart as a heart region and extracting a cusp as a reference point from the external wall shape of the heart. In this case, a processing apparatus according to this embodiment can generate analysis information concerning a cardiac disease appearing in shape by comparing the shape of the heart as a diagnostic target with the shape of the normal heart by aligning them.

In addition, the processing apparatus according to the above embodiment can generate analysis information concerning a cardiac disease appearing in the variation of the shape of the heart by performing alignment between time-series images obtained by imaging the pulsating heart and tracking heart shapes in chronological order. Furthermore, the processing apparatus according to this embodiment can generate analysis information indicating the stage of progression of a cardiac disease or the like by applying the embodiment to alignment between past and current images obtained by imaging the same case or between a plurality of past images obtained at different times. The embodiments of the present invention can also be applied to other organs such as the liver and lungs.

In addition, the use of the above embodiments is not limited to medical purposes for human organs. For example, the embodiments can also be applied to shape analysis, accuracy analysis, and the like of, for example, industrial parts. For example, when molding parts by pressing, the present invention can be applied to the comparison between the shape of a molded part and the shape of the mold. According to the present invention, even if variation in shape among molded parts is relatively large, it can be expected to robustly compare the shapes.

(Other Embodiments)

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention is not limited to the above embodiments and various changes and modifications can be made within the spirit and scope of the present invention. Therefore, to apprise the public of the scope of the present invention, the following claims are made.

The invention claimed is:

1. A processing apparatus comprising:
an obtaining unit configured to obtain, from a three-dimensional medical image of a target object, (a) a three-dimensional surface contour of the target object and (b) a reference point on the three-dimensional surface contour;
a calculation unit configured to (a) calculate a geodesic distance along the three-dimensional surface contour between the reference point and an arbitrary position on the three-dimensional surface contour, and (b) calculate an azimuth at the arbitrary position on the three-dimensional surface contour with reference to the reference point; and
a normalization unit configured to generate normalization transformation information for transforming a three-dimensional shape of a region of interest of the target object to a predetermined reference shape based on the geodesic distance and the azimuth,
wherein the transformation of the three-dimensional shape is a volumetric deformable transformation.

2. The processing apparatus according to claim 1, wherein the normalization unit generates the normalization transformation information for transforming the region of interest such that the geodesic distance and the azimuth concerning the three-dimensional shape of the region of interest substantially match the geodesic distance and the azimuth concerning the normalized shape of the region of interest based on the normalization transformation information.

3. The processing apparatus according to claim 1, wherein the normalization unit generates the normalization transformation information for transforming the three-dimensional shape of the region of interest to a rectangular shape.

4. The processing apparatus according to claim 1, wherein the normalization unit generates the normalization transformation information for transforming the three-dimensional shape of the region of interest to a shape obtained by enclosing the shape of the region of interest with a predetermined geometrical curved surface.

5. The processing apparatus according to claim 1, wherein, with processing for each of images of the region of interest of the target object imaged in a plurality of different postures,
(1) the obtaining unit obtains the plurality of three-dimensional surface contours and reference points,
(2) the calculation unit calculates the plurality of geodesic distances and azimuths, and
(3) the normalization unit generates the plurality of pieces of normalization transformation information.

6. The processing apparatus according to claim 5, further comprising a deformation unit configured to generate an image of the region of interest in another posture by deforming an image of the region of interest in at least one posture of the plurality of different postures of the target object based on the plurality of pieces of normalization transformation information.

7. The processing apparatus according to claim 6, wherein at a position corresponding to a predetermined position on the image before deformation, the deformed image has a intensity value corresponding to a intensity value at the predetermined position.

8. The processing apparatus according to claim 5, further comprising a model generation unit configured to generate a statistical deformation model representing a relationship between a plurality of regions of interest of the target object imaged in the plurality of different postures based on the plurality of pieces of normalization transformation information.

9. The processing apparatus according to claim 1, wherein the target object comprises a human body, the region of interest comprises a breast, and
wherein the obtaining unit obtains a contour of a body surface and a contour of a pectoralis major muscle surface as the contours, and obtains a nipple position as the reference point.

10. The processing apparatus according to claim 1, wherein the azimuth is an azimuth related to the target object, which can represent (1) a first direction from feet to head of the target object, (2) a second direction from abdomen to back of the target object, or (3) a third direction orthogonal to the first direction or the second direction.

11. A processing method comprising:
obtaining, from a three-dimensional medical image of a target object, (a) a three-dimensional surface contour of the target object and (b) a reference point on the three-dimensional surface contour;
calculating a geodesic distance along the three-dimensional surface contour between the reference point and an arbitrary position on the three-dimensional surface contour;
calculating an azimuth at the arbitrary position on the three-dimensional surface contour with reference to the reference point; and
generating normalization transformation information for transforming a three-dimensional shape of a region of interest of the target object to a predetermined reference shape based on the geodesic distance and the azimuth,
wherein the transformation of the three-dimensional shape is a volumetric deformable transformation.

12. A non-transitory computer-readable storage medium storing a program for causing a computer to control a processing apparatus, the program causing the computer to function as units comprising:
an obtaining unit configured to obtain, from a three-dimensional medical image of a target object, (a) a three-dimensional surface contour of the a target object and (b) a reference point on the three-dimensional surface contour;
a calculation unit configured to calculate (a) a geodesic distance along the three-dimensional surface contour between the reference point and an arbitrary position on the three-dimensional surface contour, and (b) an azimuth at the arbitrary position on the three-dimensional surface contour with reference to the reference point; and a normalization unit configured to generate normalization transformation information for transforming a three-dimensional shape of a region of interest of the target object to a predetermined reference shape based on the geodesic distance and the azimuth, wherein the transformation of the three-dimensional shape is a volumetric deformable transformation.

13. A processing apparatus comprising:

an obtaining unit configured to obtain, from a three-dimensional medical image of a target object, a reference point on a three-dimensional surface contour of the target object;

a calculation unit configured to (a) calculate a distance between the reference point and an arbitrary position on the three-dimensional surface contour, and (b) calculate a azimuth at the arbitrary position on the three-dimensional surface contour with reference to the reference point; and a normalization unit configured to generate normalization transformation information for transforming a three-dimensional shape of a region of interest of the target object to a predetermined reference shape based on the distance and the azimuth, wherein the transformation of the three-dimensional shape is a volumetric deformable transformation.

* * * * *